(12) United States Patent
Yoon et al.

(10) Patent No.: US 10,597,457 B2
(45) Date of Patent: Mar. 24, 2020

(54) EGFRVIII ANTIBODY AND COMPOSITION COMPRISING SAME

(71) Applicant: PHARMABCINE INC., Daejeon (KR)

(72) Inventors: Jae Bong Yoon, Gangwon-do (KR); Jinsang Yoo, Daejeon (KR); Jin-San Yoo, Daejeon (KR); Weon Sup Lee, Daejeon (KR); Sung-Woo Kim, Daejeon (KR); Sang Ryeol Shim, Daejeon (KR); Sang Soon Byun, Daejeon (KR); Youngae Lee, Daejeon (KR); Hyuk Joon Lee, Daejeon (KR); Do-yun Kim, Daejeon (KR); Jinhee Choi, Daejeon (KR)

(73) Assignee: PHARMABCINE INC., Daejeon (KR)

( * ) Notice: Subject to any disclaimer, the term of this patent is extended or adjusted under 35 U.S.C. 154(b) by 238 days.

(21) Appl. No.: 15/528,753

(22) PCT Filed: Nov. 25, 2014

(86) PCT No.: PCT/KR2014/011381
§ 371 (c)(1),
(2) Date: May 22, 2017

(87) PCT Pub. No.: WO2016/084993
PCT Pub. Date: Jun. 2, 2016

(65) Prior Publication Data
US 2017/0327585 A1    Nov. 16, 2017

(51) Int. Cl.
*C07K 16/30* (2006.01)
*C12N 15/13* (2006.01)
(Continued)

(52) U.S. Cl.
CPC ........ *C07K 16/2863* (2013.01); *A61K 39/395* (2013.01); *C07K 16/28* (2013.01);
(Continued)

(58) Field of Classification Search
None
See application file for complete search history.

(56) References Cited

U.S. PATENT DOCUMENTS

| 6,224,868 | B1 | 5/2001 | Wong et al. | |
| 7,628,986 | B2 * | 12/2009 | Weber | B82Y 5/00 424/130.1 |

(Continued)

FOREIGN PATENT DOCUMENTS

| JP | 2003-523771 | 8/2003 |
| KR | 10-2008-0109417 A | 12/2008 |

(Continued)

OTHER PUBLICATIONS

Kranz et al., Restricted reassociation of heavy and light chains from hapten-specific monoclonal antibodies, Proc. Natl. Acad. Sci., USA, 78(9):5807-5811, 1981.*

(Continued)

*Primary Examiner* — Claire Kaufman
(74) *Attorney, Agent, or Firm* — Hultquist, PLLC; Steven J. Hultquist

(57) ABSTRACT

The present disclosure relates to an antibody specifically binding to epidermal growth factor receptor variant III (EGFRvIII), to nucleic acid coding the antibody, to a vector comprising the nucleic acid, to a host cell, to a preparation method of the antibody, and to a pharmaceutical composition comprising the antibody as an active ingredient for treating a cancer or a tumor.

9 Claims, 11 Drawing Sheets
(10 of 11 Drawing Sheet(s) Filed in Color)
Specification includes a Sequence Listing.

(51) Int. Cl.
C07K 16/28 (2006.01)
C07K 16/46 (2006.01)
A61K 39/395 (2006.01)

(52) U.S. Cl.
CPC .............. *C07K 16/30* (2013.01); *C07K 16/46* (2013.01); *C07K 2317/21* (2013.01); *C07K 2317/34* (2013.01); *C07K 2317/56* (2013.01); *C07K 2317/565* (2013.01); *C07K 2317/77* (2013.01)

(56) References Cited

U.S. PATENT DOCUMENTS

| | | | |
|---|---|---|---|
| 9,249,217 B2 * | 2/2016 | Bigner | C07K 16/2809 |
| 10,273,309 B2 * | 4/2019 | Ellwanger | C07K 16/2809 |
| 2005/0222059 A1 | 10/2005 | Tang | |
| 2012/0115739 A1 | 5/2012 | Schmittling et al. | |
| 2014/0302062 A1 * | 10/2014 | Haynes | C07K 16/087 |
| | | | 424/159.1 |
| 2014/0314667 A1 * | 10/2014 | Hill | C07K 16/2863 |
| | | | 424/1.49 |

FOREIGN PATENT DOCUMENTS

| | | |
|---|---|---|
| KR | 2014-0024046 | 2/2014 |
| WO | 2002092771 A2 | 11/2002 |
| WO | WO03072727 A2 | 9/2003 |
| WO | 2005010151 A2 | 2/2005 |
| WO | 2005012479 A2 | 2/2005 |
| WO | 2013075048 A1 | 5/2013 |

OTHER PUBLICATIONS

Yu et al., Co-expression of EGFRvIII with ErbB-2 enhances tumorigenesis: EGFRvIII mediated constitutively activated and sustained signaling pathways, whereas EGF-induced a transient effect on EGFRmediated signaling pathways, Canc. Biol. Ther. 7: 11, 1818-1828, 2008.*

Wikstrand et al., Monoclonal antibodies against EGFRvIII are tumor specific and react with breast and lung carcinomas and malignant gliomas. Cancer Res.;55(14):3140-8, Jul. 15, 1995.*

Biernat, W., et al., "Predominant Expression of Mutant EGFR (EGFRvIII) is Rare in Primary Glioblastomas", "Brain Pathology", 2004, pp. 131-136, vol. 14.

Bonavia, R., et al., "EGFRvIII promotes glioma angiogenesis and growth through the NF-kB, interleukin-B pathway", "Oncogene", Dec. 5, 2011, pp. 4054-4066, vol. 31.

Downward, J., et al., "Close similarity of epidermal growth factor receptor and v-erb-B oncogene protein sequences", "Nature", Feb. 9, 1984, pp. 521-527, vol. 307.

Ekstrand, A.J., et al., "Genes for Epidermal Growth Factor Receptor, Transforming Growth Factor a, and Epidermal Growth Factor and Their Expression in Human Gliomas in Vivo", "Cancer Research", Apr. 15, 1991, pp. 2164-2172, vol. 51.

Fan, Q.-W., et al., "EGFR Phosphorylates Tumor-Derived EGFRvIII Driving STAT3/5 and Progression in Glioblastoma", "Cancer Cell", Oct. 14, 2013, pp. 438-449, vol. 24.

Frederick, L., et al., "Analysis of genomic rearrangements associated with EGFRvIII expression suggests involvement of Alu repeat elements", "Neuro-Oncology", May 23, 2000, pp. 159-163, vol. 2.

Gan, H.K., et al., "The epidermal growth factor receptor variant III (EGFRvIII): where wild things are altered", "FEBS Journal", Jun. 13, 2003, pp. 5350-5370, vol. 280.

Huang, P.N., et al, "Quantitative analysis of EGFRvIII cellular signaling networks reveals a combinatorial therapeutic strategy for glioblastoma", "Proceedings of the National Academy of Sciences", Jul. 31, 2007, pp. 12867-12872, vol. 104, No. 31.

Li, L., et al., "Metformin Sensitizes EGFR-TKIResistant Human Lung Cancer Cells In Vitro and In Vivo through Inhibition of IL-6 Signaling and EMT Reversal", "Clinical Cancer Research", Mar. 18, 2014, pp. 2714-2726, vol. 20, No. 10.

Oda, K., et al., "A comprehensive pathway map of epidermal growth factor receptor signaling", "Molecular Systems Biology", May 25, 2005, pp. 1-17, doi:10.1038/msb4100014.

Rich, J.N., et al., "Bone-related Genes Expressed in Advanced Malignancies Induce Invasion and Metastasis in a Genetically Defined Human Cancer Model", "The Journal of Biological Chemistry", May 2, 2003, pp. 15951-15957 vol. 278, No. 18.

Shi, Q., et al., "Single-cell proteomic chip for profiling intracellular signaling pathways in single tumor cells", "Proceedings of the National Academy of Sciences", Jan. 10, 2012, pp. 419-424, vol. 109, No. 2.

Tanaka, K., et al., "Oncogenic EGFR Signaling Activates an mTORC2NF-kB Pathway That Promotes Chemotherapy Resistance", "Cancer Discovery", Sep. 13, 2011, pp. 524-538, vol. 1.

Zhang, H., et al., "ErbB receptors: from oncogenes to targeted cancer therapies", "The Journal of Clinical Investigation", Aug. 2007, pp. 2051-2058, vol. 117, No. 8.

Gupta, P., et al., "Development of an EGFTvIII Specific Recombinant Antibody", "BMC Biotechnology", 2010, p. 1-13, vol. 10, No. 72.

Hills, D., et al., "Specific Targeting of a Mutant, Activated EGF Receptor Found in Glioblastoma Using a Monoclonal Antibody", "Int J. Cancer", 1995, pp. 537-543, vol. 63.

Okamoto, S., et al., "Monoclonal Antibody Against the Fusion Junction of a Deletion-Mutant Epidermal Growth Factor Receptor", "British Journal of Cancer", 1996, pp. 1366-1372, vol. 73.

Safdari, Y., et al., "humMRI, a Highly Specific Humanized Single Chain Antibody for Targeting EGFRvIII", "International Immunopharmacology", 2014, pp. 304-310, vol. 18.

* cited by examiner

Fig. 2

| Drug | Mechanism of Action | Disease Area | Clinical Trials | FDA Approval Status |
|---|---|---|---|---|
| Erlotinib (Tarceva), gefitinib (Iressa) (receptor tyrosine kinase inhibitors) | Inhibits GTP-binding site of EGFR | NSCLC (EGFR-mutated) | Phase III 1st line | Stage IV/metastatic, as a single agent or maintenance |
| | | Pancreas | Phase III 1st line (erlotinib + gemcitabine [Gemzar] vs gemcitabine | |
| Crizotinib (Xalkori) (receptor tyrosine kinase inhibitor) | Inhibits ATP-binding site of fusion proteins | NSCLC (EML4-, ALK-, and ROS-mutated) | Phase II 2nd line | Stage IV/metastatic, as a single agent |
| Cetuximab (Erbitux), panitumumab (Vectibix) (monoclonal antibodies to EGFR) | Anti-EGFR | NSCLC | Cetuximab: Phase III 1st line | Stage IV metastatic, in combination with platinum and vinorelbine |
| | | Colon | Phase II 1st line | Stage IV metastatic disease if KRAS mutation–negative |
| Trastuzumab (Herceptin) | Anti-HER2 | Breast | Phase III 1st line | Any HER2-positive breast cancer patient receiving adjuvant or palliative chemotherapy |
| Pertuzumab (Perjeta) | Anti-HER2 with linked maytansine | Breast | Phase III | Stage IV disease |

ATP = adenosine triphosphate; GTP = guanosine triphosphate; HER2 = human epidermal growth factor receptor 2; NSCLC = non-small-cell lung cancer.

Fig. 5

| Condition | Intervention | Phase |
|---|---|---|
| Glioblastoma<br>Gliosarcoma<br>Glioblastoma With Oligodendroglial Component | Drug: Bevacizumab<br>Drug: Rindopepimut (CDX-110, Celldex Therapeutics) with GM-CSF<br>Drug: KLH | Phase 2 |
| Patients With Residual or Reccurent EGFRvIII+ Glioma | Biological: CART-EGFRvIII T cells | Phase 1 Pilot Study |
| Malignant Glioma<br>Glioblastoma<br>Brain Cancer | Biological: Anti-EGFRvIII CAR transduced PBL<br>Drug: Aldesleukin<br>Drug: Fludarabine<br>Drug: Cyclophosphamide | Phase 1<br>Phase 2 |
| Glioblastoma<br>Gliosarcoma<br>Glioblastoma With Oligodendroglial Component | Drug: Rindopepimut (CDX-110) with GM-CSF<br>Drug: Temozolomide<br>Drug: KLH | Phase 3 |
| Advanced Malignant Glioma<br>GBM | Drug: AMG 595 (Amgen) | Phase 1<br>(FIH) |
| Astrocytic Tumors<br>GBM<br>Anaplastic Astrocytoma<br>Brain Tumor | Biological: Cohort 1<br>Biological: Cohort 2<br>Biological: Cohort 3<br>Drug: Antibiotics | Phase 1 |
| Malignant Glioma | Drug: CDX-110 with GM-CSF<br>Drug: temozolomide | Phase 2 |
| Advanced Solid Tumors | Drug: ABT-806 (Abott) | Phase 1 |

Bead panning monophage ELISA

EGFRVIII ANTIBODY AND COMPOSITION COMPRISING SAME

CROSS-REFERENCE TO RELATED APPLICATION

This application is a U.S. national phase under the provisions of 35 U.S.C. § 371 of International Patent Application No. PCT/KR2014/011381 filed Nov. 25, 2014. The disclosure of such international patent application is hereby incorporated herein by reference in its entirety, for all purposes.

TECHNICAL FIELD

The present disclosure relates to an antibody specifically binding to epidermal growth factor receptor variant III (EGFRvIII), a nucleic acid coding the antibody, a vector including the nucleic acid, a host cell including the vector, a preparation method of the antibody, and a pharmaceutical composition for treating cancer or tumors including the antibody as an active ingredient.

DESCRIPTION OF THE RELATED ART

The EGFR (Epidermal growth factor receptor; ErbB-1; HER1 in humans) is a receptor tyrosine kinase (RTK) of the ErbB family expressed on the surface of cells found by Stanley Cohen of Vanderbilt University. Overexpression or overactivity mutations of the receptor acts as cancerization (Zhang H. et al, 2007). The receptors of the EGFR family (EGFR (ErbB-1), HER2/c-neu (ErbB-2), Her 3 (ErbB-3) and Her 4 (ErbB-4)) are reacted in a ligand such as EGF, TGF-α and the like (in the case of Her2, there is no known ligand) to form a homo- or heterodimer and transmit an activation signal to cells.

By virtue of the dimer formation, the signal that goes through MAPK, Akt or JNK through autophosphorylation (Downward J. et al., 1984) as illustrated in the picture is transmitted to activate cell cycle or cell proliferation (Oda K. et al., 2005). Each domain and phosphorylation site of the EGFR is the same as illustrated in FIG. 1.

Various therapies for inhibiting the activation of the tumor-related EGFR have been emerged and now show a strong anticancer effect. New types of EGFR antagonists are being developed to compensate shortcomings such as side effects, tolerances and the like according to therapies. The details of the EGFR antagonist currently in development are the same as described in FIG. 2.

The EGFR overexpression and mutations come in many different forms in lung cancer, anal cancer, and glioblastoma multiforme (GBM). The EGFRvIII mutations are often found in a brain tumor, and reflect a poor prognosis after a treatment through surgery, radiation therapy, and chemotherapy (Kuan C T et al., 2003). The EGFR mutants in the form of a recombination have deletions or duplications of specific exons. The EGFR and the EGFR mutants in the form of a recombination are the same as illustrated in FIG. 3.

EGFRvIII is an EGFR variant of SEQ ID NO: 1, which is most frequently appeared and lacks amino acids in exons 2-7, and is expressed in 50% or more of terminally ill brain tumor patients. EGFRvIII lacks 267 amino acids in the amino acid sequence of EGFRwt, binds to exons 1 and 8 and produces glycine, which is a new amino acid, and induces phosphorylation of the intracellular domain and shows continuous activity, thereby contributing to the carcinogenesis (Downward J et al., 1984). Of course, other forms of EGFR can also be targeted, but at the present time, EGFRvIII is regarded as the most suitable EGFR variant as an anticancer target, and many researches and developments are ongoing.

In particular, in brain tumors, cell signals are transmitted by the main signaling pathway mainly via PI3K and AKT of EGFRvIII. Through the activation of Stat-3, AP-1 or MAPK as a minor pathway, it contributes to cancer cell proliferation, resistance to apoptosis, angiogenesis, increase of penetration of cancer cells, formation of cancer stem cells, and the like (Gan H K, et al., 2013). Recent studies have reported that EGFRvIII plays an important role in carcinogenesis by activating NF-κB via mTORC2 (Bonavia et al., 2012; Tanaka et al., 2011). The signaling pathway according to the activation of EGFRvIII is the same as illustrated in FIG. 4.

In addition, since EGFRvIII induces activation following c-Met phosphorylation (Huang P H. et al., 2007), when it is applied and administered to a patient in combination with a c-Met inhibitor together with an EGFR or EGFRvIII inhibitor, it may improve efficacy while reducing the resistance to chemotherapy of a patient with high levels of EGFRvIII.

EGFRvIII is usually expressed in brain tumors simultaneously with EGFR wild-type (WT) (Ekstrand et al., 1991), and since EGFRvIII itself is expressed in EGFR gene amplified tumors (Biernat et al., 2004, Frederick et al., 2000), it has been thought that the individual cancer cells would simultaneously perform EGFRwt amplification and EGFRvIII expression for interaction.

EGFRvIII is expressed at relatively high frequency in brain tumors, but further studies are needed in other carcinomas. A recent study using brain tumor cell lines transformed to express EGFRvIII revealed that networks using EGFRvIII and EGFRwt could surely have the possibility of being co-activated (Shia Q. et al., PNAS, 2012). Such interaction between EGFRvIII and EGFRwt needs to be confirmed again using EGFRvIII which is expressed naturally through xenografts model, GBM spheroid lines or other cell lines.

It has been reported that EGFR phosphorylates EGFRvIII and leads a STAT3/5 activation pathway, and greatly affects the progression of brain tumors (Fan Q W et al., 2013). EGFRvIII dimer formation greatly affects the activation of signal transduction. As the expression of EGFRwt increases, the phosphorylation and activation of EGFRvIII are enhanced. Thus, it is believed that dimerization arm and kinase activity, which form the dimerization of EGFRwt, contribute to the activation of EGFRvIII. From the result that the cancerization induced by EGFRvIII is inhibited when the expression of EGFRwt or HB-EGF is inhibited in an orthotopic transplantation model (Li L. et al., 2014), it can be said that the activation pathway surrounding EGFRwt plays a very important role in tumorigenesis via activation of EGFRvIII.

Currently, the therapeutic agents to treat (brain) tumors that are being developed while being targeted to EGFRvIII can be divided into five categories. The first one is a method of blocking the internal signal transduction of EGFRwt and EGFRvIII by using the conventional EGFR therapeutic agents. The second one is a method of inhibiting the interaction between external signal transduction and receptors by using antibodies that simultaneously target EGFR and EGFRvIII, such as ABT-806 (mAb806, Abbott). The third one is the development of an anti-EGFRvIII antibody in the form of an antibody drug conjugate (ADC), as AMG-595 which is now being developed by Amgen. The fourth one is that the form of Chimeric Antigen receptor-T cell (CAR-T) may be used as a cell immunotherapeutic agent. The fifth one is a method of joining EGFRvIII specific 14 amino acid sequences to Keyhole limpet hemocyanin (KLH) and administering it as an EGFRvIII anti-cancer vaccine. There is currently no commercialized anticancer drug targeting only EGFRvIII, not EGFR. As illustrated in FIG. 5, there is an EGFRvIII vaccine CDX-110 which is now being developed by Celldex Therapeutics which leads in clinical development.

Under these technical backgrounds, the inventors of the present disclosure prepared a novel antibody specifically binding to EGFRvIII. In particular, they confirmed that a novel antibody that binds only to EGFRvIII, but not to EGFRwt, can be prepared by producing it to specifically bind to EGFRvIII without cross-reacting with EGFRwt, and completed the present disclosure.

SUMMARY

It is an object of the present disclosure to provide a novel antibody specifically binding to EGFRvIII, a nucleic acid coding the antibody, a vector including the nucleic acid, a host cell including the vector, a preparation method thereof, and a pharmaceutical composition for treating cancer or tumors including the antibody as an active ingredient.

The present disclosure relates to an antibody binding to epidermal growth factor receptor variant III (EGFRvIII) comprising an amino acid sequence of SEQ ID NO: 1, free from cross-reacting with wild-type epidermal growth factor receptor (EGFR), wherein the antibody is specifically binding to the $1^{st}$ to $13^{th}$ amino acid regions of the amino acid sequence of SEQ ID NO: 1.

The present disclosure relates to a nucleic acid coding the antibody.

The present disclosure relates to a vector including the nucleic acid.

The present disclosure relates to a host cell including the vector.

The present disclosure relates to a preparation method of the antibody including expressing the antibody by culturing the host cell.

The present disclosure relates to a pharmaceutical composition for treating cancer or tumors including the antibody as an active ingredient.

The present disclosure relates to a method for treating cancer or tumors by administering the antibody to an individual in need thereof in a pharmacologically effective amount.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 illustrates the development progress of the known antagonists targeting EGFR receptors.

FIG. 5 illustrates a candidate list of EGFRvIII targeting therapeutic agents under clinical development obtained from www.clinicaltrials.gov.

DETAILED DESCRIPTION OF THE EMBODIMENT

Figure 1:
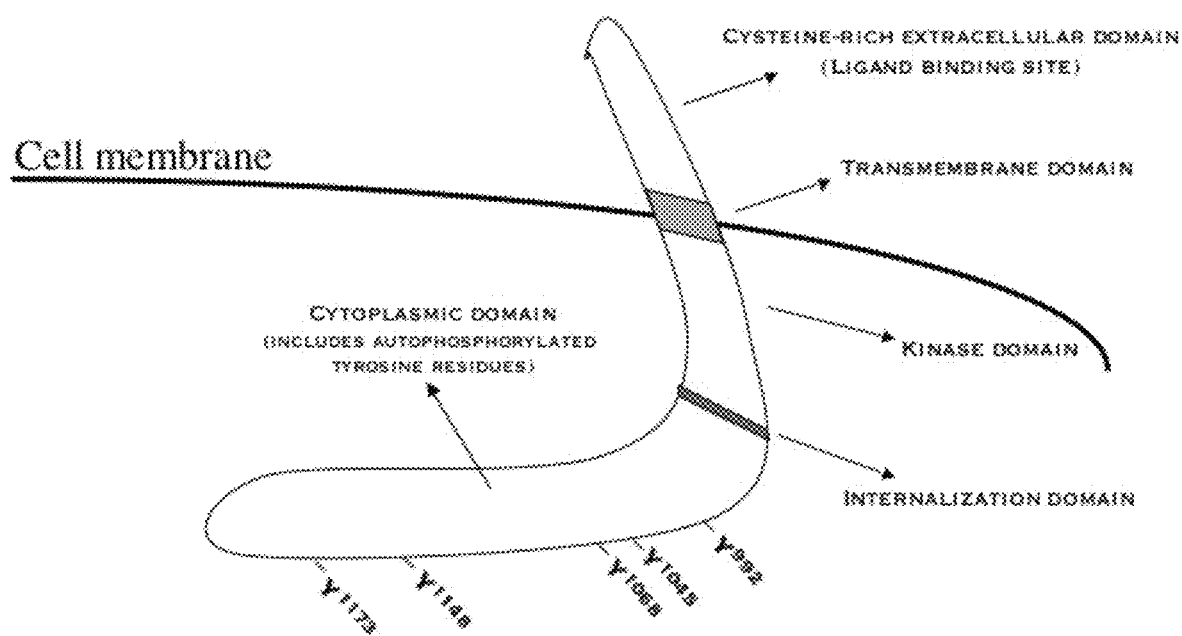
FIG. 1 illustrates each domain and phosphorylation site of the EGFR.
Figure 3:
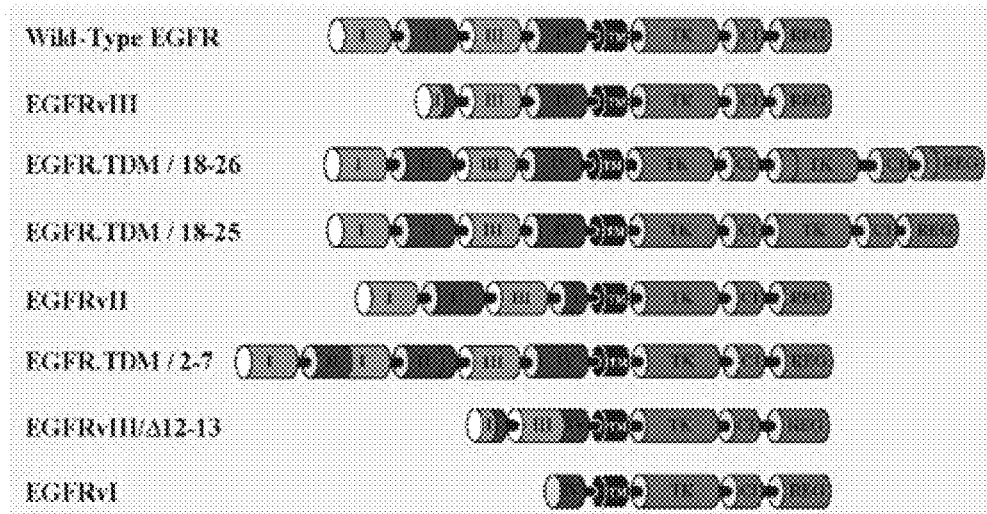
FIG. 3 is a schematic diagram illustrating the structure of EGFR mutants in a recombinant form with EGFR.
Figure 4:
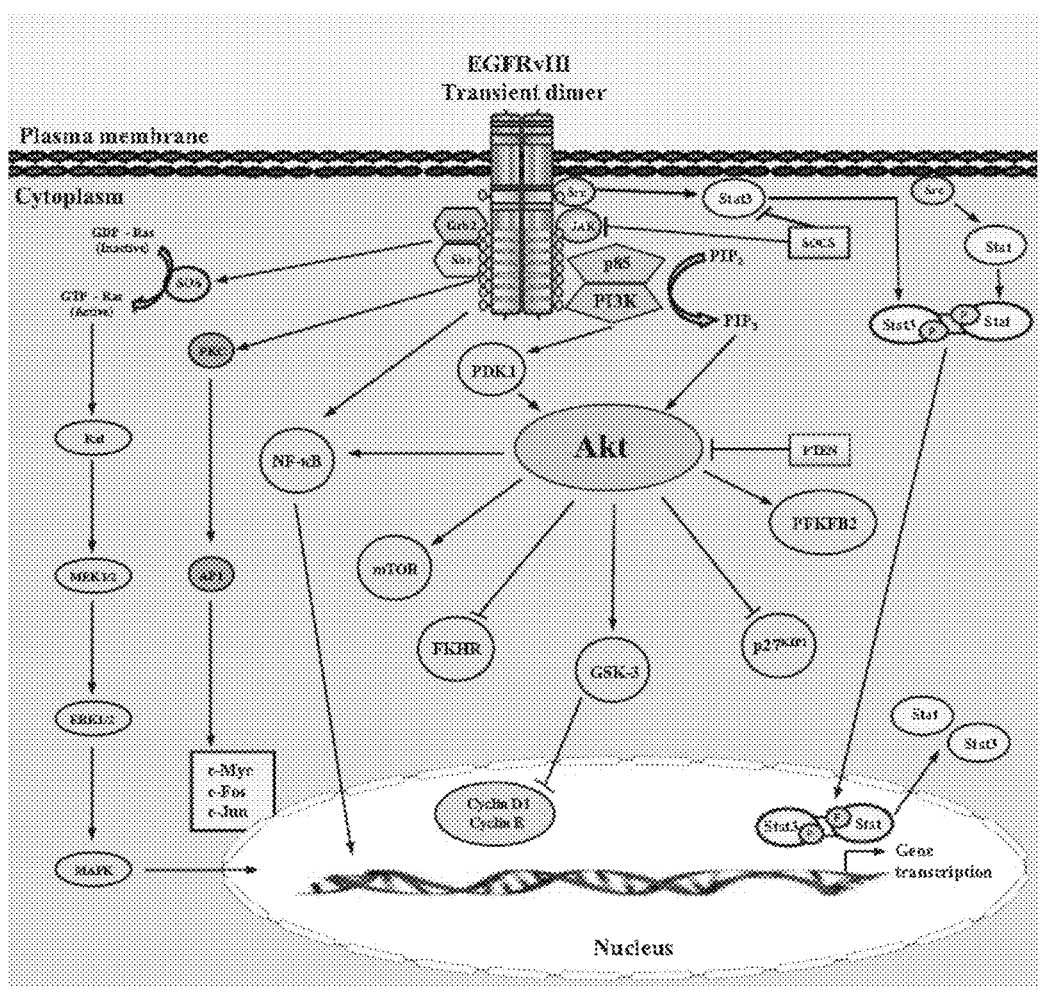
FIG. 4 is a schematic diagram illustrating the signal transduction flow according to the activation of EGFRvIII.

In one aspect, the present disclosure relates to an antibody binding to epidermal growth factor receptor variant III (EGFRvIII) comprising an amino acid sequence of SEQ ID NO: 1, free from cross-reacting with wild type epidermal growth factor receptor (EGFR), wherein the antibody is specifically binding to the $1^{st}$ to $13^{th}$ amino acid regions of the amino acid sequence of SEQ ID NO: 1. The detailed descriptions of each constitution are as follows.

Antigen EGFRvIII

As discussed above, EGFRvIII is a deletion mutant of EGFR in which 267 amino acids are deleted in the extracellular domain of EGFR together with a single amino acid substitution of glycine at a junction, and has a sequence of SEQ ID NO: 1.

The inventors of the present disclosure produced an antibody by using a peptide including an EGFRvIII peptide specific sequence 13mer as an antigen in order to produce an antibody specifically binding to EGFRvIII without cross-reacting with the EGFR wild type. Specifically, the antibody according to the present disclosure may specifically bind to the sequence of SEQ ID NO: 2 LEEKKGNYVVTDHC-SGGKN (N is biotin) in which linker and biotin of EGFRvIII peptide specific sequences 13mer, 4mer are included. At the same time, a peptide having a sequence of TTACCDRII, for example, SEQ ID NO: 3 NEINPGNGHT-NYNEKFKS (N is biotin) was used as a negative antigen to block non-specific binding. Through this, an antibody specifically binding to EGFRvIII without cross-reacting with the EGFR wild type was produced.

Antibody

The term "antibody" used in the present specification refers to an immunoglobulin molecule that is immunologically reactive with a specific antigen, means a protein molecule that serves as a receptor that specifically recognizes an antigen, and may includes both polyclonal and monoclonal antibodies and whole antibodies and antibody fragments. In addition, it may also include chimeric antibodies (e.g., humanized murine antibodies) and bivalent or bispecific molecules (e.g., bispecific antibodies), diabodies, triabodies and tetrabodies.

The whole antibody is a structure having two overall length light chains and two overall length heavy chains, and each light chain is linked to a heavy chain by a disulfide bond. The whole antibody includes IgA, IgD, IgE, IgM and IgG, and IgG is a subtype and includes IgG1, IgG2, IgG3 and IgG4. The antibody fragment means a fragment having an antigen-binding function, and includes Fab, Fab', F (ab')2, Fv, and the like.

The Fab has one antigen-binding site in a structure having a variable region of a light chain and a heavy chain, a constant region of a light chain, and a first constant region (CH1 domain) of a heavy chain. Fab' differs from Fab in that it has a hinge region that contains at least one cysteine residue at the C-terminal of the heavy chain CH1 domain. The F(ab')2 antibody is generated when the cysteine residue of the hinge region of the Fab' forms a disulfide bond.

The variable fragment (Fv) means the minimum antibody fragment having only a heavy chain variable region and a light chain variable region. The double-stranded Fv (dsFv) is linked by a disulfide bond to a heavy chain variable region and a light chain variable region. Single chain Fv (scFv) is generally linked to a variable region of a heavy chain and a variable region of a light chain through a peptide linker by a covalent bond. Such antibody fragments may be obtained using protein hydrolytic enzymes (for example, Fab may be obtained by restricting and cutting the whole antibody with papain and F(ab')2 fragments may be obtained by cutting it with pepsin), and may be produced through gene recombinant technology (e.g., setting DNA coding the heavy chain of the antibody or its variable region and DNA coding the light chain or its variable region as a template, amplifying them by the PCR using a primer pair, and combining and amplifying the DNA coding a peptide linker and a primer pair configured to link each of the both terminals to the heavy chain and its variable region and the light chain or its variable region).

Immunoglobulins have a heavy chain and a light chain, and each heavy and light chain includes a constant region and a variable region (the site is also known as a domain). The variable regions of the light and heavy chains include three variable regions and four framework regions which are called as complementarity-determining regions (hereinafter, referred to as "CDR"). The CDR serves as the binding mainly to the epitope of an antigen. The CDRs of each chain are typically called sequentially as CDR1, CDR2, CDR3 starting from the N-terminus, and are identified by the chain in which a specific CDR is located.

The term "monoclonal antibody" used in the present specification means an antibody molecule of a single molecular composition obtained from a substantially identical antibody group, and may exhibit a single binding specificity and affinity for a specific epitope.

The term "human antibody" used in the present specification refers to a molecule derived from human immunoglobulin, wherein all of the amino acid sequences constituting the antibody including a complementarity-determining region and a framework region are composed of the amino acid sequence of human immunoglobulin. The human antibody is usually used for treating human diseases, and has advantages in that i) target cells may be more efficiently destroyed by interacting with the human immune system more stably, for example, by complement-dependent cytotoxicity (CDC) or antibody-dependent cellmediated cytotoxicity (ADCC), ii) the human immune system does not recognize the antibody as a foreign one, and iii) even if a less amount of drugs is administrated less frequently, a half-life in a human circulatory system is similar to a naturally occurring antibody.

In consideration of the above, the antibody according to the present disclosure is a monoclonal antibody specifically binding to EGFRvIII, which not only exhibits excellent affinity and specificity for EGFRvIII but also exhibits low immunogenicity because it is derived from human, and thus is suitable for the treatment of diseases such as cancer or tumors.

The term "antibody specifically binding to EGFRvIII" used in the present specification means an antibody that binds to EGFRvIII and inhibits the biological activity of EGFRvIII, and can be used interchangeably with an anti-EGFRvIII antibody. At this time, the $K_D$ for the EGFRvIII may be, for example, $10^{-8}$ or less, preferably $10^{-9}$ or less, more preferably $10^{-10}$ or less.

The term "without cross-reacting with EGFR" used in the present specification may mean that an antibody that binds to the EGFR wild type and an antibody that binds to EGFRvIII do not show cross reactivity to each antigen. At this time, the antibody that does not cross-react with the EGFR may have, for example, $10^{-5}$ or more, preferably $10^{-4}$ or more, more preferably $10^{-3}$ or more of $K_D$ of the antibody against the EGFR wild type. Substantially, the antibody that does not cross-react with the EGFR may mean an antibody that cannot detect an antibody that binds to the EGFR wild type in an unlimited form of a standard binding assay.

In one exemplary embodiment, the antibody according to the present disclosure may be, for example, as specifically described in Example 1, the monoclonal human antibodies PA430, PD27, PD52 and PD10 that do not cross-react with the EGFR, and are structurally specified and separated to be specifically bound to the region of $1^{st}$ to $13^{th}$ amino acids regions among the amino acid sequences of EGFRvIII of SEQ ID NO: 1. The amino acid sequences for heavy chain CDRs and light chain CDRs of each antibody are as listed in the following Tables 1 and 2.

TABLE 1

| Ab | H-CDR1 | H-CDR2 | H-CDR3 |
|---|---|---|---|
| PA430 | YHAMH (SEQ ID NO: 4) | AMSHDGTETSYADSVKG (SEQ ID NO: 8) | EGLRSNGGAFET (SEQ ID NO: 12) |
| PD52 | DYAMH (SEQ ID NO: 5) | GISWNSGAIGYADSVKG (SEQ ID NO: 9) | ASRGLGDAFDI (SEQ ID NO: 13) |
| PD27 | EHAMH (SEQ ID NO: 6) | GINWNSGKTGYADSVKG (SEQ ID NO: 10) | PGEDTGGGFDI (SEQ ID NO: 14) |
| PD10 | EHAMH (SEQ ID NO: 7) | GINWNSGKTGYADSVKG (SEQ ID NO: 11) | PGEDTGGGFDI (SEQ ID NO: 15) |

TABLE 2

| Ab | L-CDR1 | L-CDR2 | L-CDR3 |
|---|---|---|---|
| PA430 | SGDVLPKHYAY (SEQ ID NO: 16) | KDSERPS (SEQ ID NO: 20) | QSVDSSDTSVV (SEQ ID NO: 24) |
| PD52 | SGDVLPKHYAY (SEQ ID NO: 17) | KDTERPS (SEQ ID NO: 21) | QSVDNSDTSVV (SEQ ID NO: 25) |
| PD27 | SGDVLADHYSY (SEQ ID NO: 18) | KDSERPS (SEQ ID NO: 22) | QSVDSSDTSVV (SEQ ID NO: 26) |
| PD10 | SSDVGGYNYVS (SEQ ID NO: 19) | DVTKRPS (SEQ ID NO: 23) | SSYSSSTFYV (SEQ ID NO: 27) |

The antibody according to the present disclosure may be formed, for example, by mixing $V_H$ and $V_L$ sequences, which are structurally similar as to the $V_H$ CDR1, 2 and 3 sequences and $V_L$ CDR1, 2 and 3 sequences described in Tables 1 and 2, and by being placed as CDR1, 2 and 3 of $V_H/V_L$ pairing, and may include, for example, a heavy chain variable region comprising the following heavy chain CDRs:

a heavy chain CDR1 comprising at least one amino acid sequence selected from the group consisting of SEQ ID NOS: 4-7;

a heavy chain CDR2 comprising at least one amino acid sequence selected from the group consisting of SEQ ID NOS: 8-11; and a heavy chain CDR3 comprising at least one amino acid sequence selected from the group consisting of SEQ ID NOS: 12-15.

In addition, the antibody according to the present disclosure may include a light chain variable region comprising the following light chain CDRs:

a light chain CDR1 comprising at least one amino acid sequence selected from the group consisting of SEQ ID NOS: 16-19;

a light chain CDR2 comprising at least one amino acid sequence selected from the group consisting of SEQ ID NOS: 20-23; and a light chain CDR3 comprising at least one amino acid sequence selected from the group consisting of SEQ ID NOS: 24-27.

In one embodiment, the antibody according to the present disclosure may specifically include an amino acid sequence of a heavy chain variable region and a light chain variable region as described in Table 3 below, or a sequence having homology thereto:

TABLE 3

| Ab | Variable Region | Amino acid sequence |
|---|---|---|
| PA430 | VH (SEQ ID NO: 28) | QMQLVESGGGVVQPGKSLRLSCAASGFTFSYHA MHWVRQAPGKGLEWLAAMSHDGTETSYADSV KGRITISRDNSKSALYLQMNSLRAEDTAVYYCTA EGLRSNGGAFETWGRGTMITVSS |
|  | VL (SEQ ID NO: 32) | SYELTQPPSVSVAPGQTARITCSGDVLPKHYAYW YQQKPGQAPVLVIYKDSERPSGIPERFTGSSSGTK VTLTISGVRAEDEADYYCQSVDSSDTSVVFGGGT KLTVLG |
| PD52 | VH (SEQ ID NO: 29) | QMQLVQSGGGVVQPGGSLRLSCVGSGFSFDDYA MHWVRQAPGKGLEWVSGISWNSGAIGYADSVK GRFTVSRDNSKNSLYLQMNSLRAEDTAVYYCAT ASRGLGDAFDIWGQGTMVTVSS |
|  | VL (SEQ ID NO: 33) | SYELTQPPSVSVSPGQTARITCSGDVLPKHYAYW YQQKPGQAPVLVIYKDTERPSGIPERFSGSSSGTT VTLTISGVQAEDEADYYCQSVDNSDTSVVFGGG TKLTVLG |
| PD27 | VH (SEQ ID NO: 30) | QVQLVESGGGLVQPGGSLRLSCAASGFTFDEHA MHWVRQAPGKGLQWVSGINWNSGKTGYADSV KGRFTISRDNSKNSLYLQMNSLRAEDTAVYYCTR PGEDTGGGFDIWGQGTMITVSS |
|  | VL (SEQ ID NO: 34) | SYELTQPLSVSVSPGQTARITCSGDVLADHYSYW YQQKPGQAPVLVMYKDSERPSGIPERFSGSSSGT TVTLTISGVQAEDEADYYCQSVDSSDTSVVFGGG TKLTVLG |
| PD10 | VH (SEQ ID NO: 31) | QVQLVESGGGLVQPGGSLRLSCAASGFTFDEHA MHWVRQAPGKGLQWVSGINWNSGKTGYADSV KGRFTISRDNSKNSLYLQMNSLRAEDTAVYYCTR PGEDTGGGFDIWGQGTMITVSS |
|  | VL (SEQ ID NO: 35) | NFMLTQPASVSGSPGQSITISCTGSSSDVGGYNYV SWYQQHPGKAPQLIIYDVTKRPSGVSNRFSGSKS GNSASLTISGLQAEDEADYYCSSYSSSTFYVFGTG TKVTVLG |

The antibody according to the present disclosure may include, for example, a heavy chain variable region comprising a sequence having at least 80% of homology with at least one amino acid sequence selected from the group consisting of SEQ ID NOS: 28-31. The antibody may include, i.e., the sequences of SEQ ID NOS: 28-31, as heavy chain variable regions, comprising a sequence having at least 80% of homology, preferably at least 90%, at least 95%, at least 97%, at least 98%, and at least 99% of homology, and more preferably 100% of homology with at least one amino acid sequence selected from the group consisting of SEQ ID NOS: 28-31.

In addition, the antibody according to the present disclosure may comprise a light chain variable region comprising a sequence having at least 80% of homology with at least one amino acid sequence selected from the group consisting of SEQ ID NOS: 32-35. The antibody may include i.e., the sequences of SEQ ID NOS: 32-35 as light chain variable regions comprising a sequence having at least 80% of homology, preferably at least 90%, at least 95%, at least 97%, at least 98%, and at least 99% of homology, and more preferably 100% of homology with at least one amino acid sequence selected from the group consisting of SEQ ID NOS: 32-35.

To be specific, the antibody according to the present disclosure may include the following heavy chain variable region and light chain variable region selected from the group consisting of the following, and the $V_H$ sequence and $V_L$ sequence described in Table 3 may be formed by mixing $V_H$ and $V_L$ sequences, which are structurally similar and by being placed as $V_H/V_L$ pairing without limitation:

A heavy chain variable region comprising a sequence of SEQ ID NO: 28 and a light chain variable region of the sequence selected from the group consisting of SEQ ID NOS: 32-35;

A heavy chain variable region comprising a sequence of SEQ ID NO: 29 and a light chain variable region of the sequence selected from the group consisting of SEQ ID NOS: 32-35;

A heavy chain variable region comprising a sequence of SEQ ID NO: 30 and a light chain variable region of the sequence selected from the group consisting of SEQ ID NOS: 32-35;

A heavy chain variable region comprising a sequence of SEQ ID NO: 31 and a light chain variable region of the sequence selected from the group consisting of SEQ ID NOS: 32-35.

In particular, the antibody according to the present disclosure may include the following heavy chain variable region and light chain variable region:

A heavy chain variable region comprising a sequence of SEQ ID NO: 28 and a light chain variable region comprising a sequence of SEQ ID NO: 32;

A heavy chain variable region comprising a sequence of SEQ ID NO: 29 and a light chain variable region comprising a sequence of SEQ ID NO: 33.

A heavy chain variable region comprising a sequence of SEQ ID NO: 30 and a light chain variable region comprising a sequence of SEQ ID NO: 34; and A heavy chain variable region comprising a sequence of SEQ ID NO: 31 and a light chain variable region comprising a sequence of SEQ ID NO: 35.

In another aspect, the present disclosure relates to nucleic acid coding the antibody. The term "nucleic acid" used in the present specification may be present in a cell, a cell lysate, or in a partially purified form or in a substantially pure form. The nucleic acid becomes "isolated" or "substantially pure" when purified from other cell components or other contaminants, for example, nucleic acid or proteins of the other cells by the standard technology including alkaline/SDS treatment, CsCl banding, column chromatography, agarose gel electrophoresis and the others that are well known in the pertinent art. The nucleic acid of the present disclosure may be, for example, DNA or RNA, and may or may not include an intron sequence.

In one exemplary embodiment, the nucleic acid according to the present disclosure coding the $V_H$ sequence and the $V_L$ sequence is described in Table 4, and may include at least one sequence coding a heavy chain variable region having at least 95% of homology with a sequence coding heavy chain variable region selected from the group consisting of SEQ ID NOS: 36-39 and/or may include at least one sequence coding a light chain variable region having at least 95% of homology with a sequence coding at least one light chain variable region selected from the group consisting of SEQ ID NOS: 40-43. The antibody has at least 95% of homology, preferably at least 98% of homology, more preferably 100% of homology with at least one nucleic acid sequence selected from the group consisting of SEQ ID NOS: 36-39 and/or SEQ ID NOS: 40-43.

TABLE 4

| Ab | Variable Region | Nucleic acid sequence |
|---|---|---|
| PA430 | VH (SEQ ID NO: 36) | CAGATGCAGCTGGTGGAGTCCGGGGGAGGCGTGG TCCAGCCTGGGAAGTCCCTGAGACTTTCCTGTGC AGCGTCTGGATTCACCTTCAGTTACCATGCCATGC ACTGGGTCCGCCAGGCTCCAGGCAAGGGGCTGGA GTGGCTGGCAGCTATGTCACATGATGGAACCGAA ACCAGCTACGCAGACTCCGTGAAGGGCCGAATCA CCATCTCCAGAGACAATTCCAAGAGTGCGTTGTAT CTACAAATGAACAGTCTGAGAGCCGAGGACACGG CCGTGTATTACTGTACCGCAGAGGGGCTTCGGAGC AATGGAGGGGCTTTTGAGACTTGGGGCCGCGGGA CAATGATCACCGTCTCCTCA |
| | VL (SEQ ID NO: 40) | TCCTATGAGCTGACACAGCCACCCTCAGTGTCGGT GGCCCCAGGGCAGACGGCCAGGATCACCTGCTCT GGAGATGTACTGCCAAAACATTATGCTTATTGGTA CCAGCAGAAGCCAGGCCAGGCCCCTGTTTTGGTG ATATATAAAGACAGCGAGAGGCCCTCAGGGATCCC TGAGCGATTCACTGGTTCCAGCTCAGGGACAAAA GTCACGCTGACCATAAGTGGAGTCCGGGCAGAAG ACGAGGCTGACTATTATTGTCAATCAGTAGACAGC AGTGATACTTCTGTGGTTTTCGGCGGAGGGACCAA GCTGACCGTCCTAGGT |
| PD52 | VH (SEQ ID NO: 37) | CAGATGCAGCTGGTGCAGTCTGGAGGGGGCGTGG TACAGCCTGGGGGGTCCCTGAGACTCTCCTGTGTA GGCTCTGGATTCAGCTTTGATGATTATGCCATGCAC TGGGTCCGTCAGGCTCCAGGGAAGGGCCTGGAGT GGGTCTCAGGTATTAGTTGGAATAGTGGTGCCATA |

TABLE 4-continued

| Ab | Variable Region | Nucleic acid sequence |
|---|---|---|
| | VL<br>(SEQ ID NO: 41) | GGCTATGCGGACTCTGTGAAGGGCCGATTCACCGT<br>CTCCAGAGACAACAGCAAAAACTCCCTGTATCTG<br>CAAATGAACAGTCTGAGAGCCGAGGACACGGCCG<br>TGTATTACTGTGCCACAGCCTCCAGAGGACTTGGT<br>GATGCTTTTGATATCTGGGGCCAGGGGACAATGGT<br>CACCGTCTCCTCA<br>TCCTATGAGCTGACACAGCCCCCCTCGGTGTCAGT<br>GTCCCCAGGACAGACGGCCAGGATCACCTGCTCT<br>GGAGATGTACTGCCAAAACATTATGCTTATTGGTA<br>CCAGCAGAAGCCAGGCCAGGCCCCTGTTTTGGTG<br>ATATATAAAGACACTGAGAGGCCCTCAGGGATCCC<br>TGAGCGATTCTCTGGCTCCAGTTCAGGGACAACA<br>GTCACGTTGACCATCAGTGGAGTCCAGGCAGAAG<br>ACGAGGCTGACTATTATTGTCAATCAGTAGACAAC<br>AGTGATACTTCTGTGGTTTTCGGCGGAGGGACCAA<br>GCTGACCGTCCTAGGT |
| PD27 | VH<br>(SEQ ID NO: 38) | CAGGTGCAGCTGGTGGAGTCTGGGGGAGGCTTGG<br>TACAGCCTGGAGGGTCCCTGAGACTCTCCTGTGC<br>AGCCTCTGGATTCACCTTTGATGAACATGCCATGC<br>ACTGGGTCCGGCAAGCTCCAGGGAAGGGCCTGCA<br>GTGGGTCTCAGGAATCAATTGGAATAGTGGTAAAA<br>CAGGCTATGCGGACTCTGTGAAGGGCCGATTCACC<br>ATCTCCAGAGACAACAGCAAAAACTCCCTGTATCT<br>GCAAATGAACAGTCTGAGAGCCGAGGACACGGCC<br>GTGTATTACTGTACTAGACCCGGGGAGGACACCGG<br>GGGTGGCTTTGATATCTGGGGCCAAGGGACAATGA<br>TCACCGTCTCCTCA |
| | VL<br>(SEQ ID NO: 42) | TCCTATGAGCTGACTCAGCCACTCTCGGTGTCAGT<br>GTCCCCAGGACAGACGGCCAGGATCACCTGCTCT<br>GGAGATGTATTGGCAGATCATTATTCTTATTGGTAC<br>CAGCAGAAGCCAGGCCAGGCCCCTGTGTTGGTGA<br>TGTATAAAGACAGTGAGAGGCCCTCTGGGATCCCT<br>GAGCGATTCTCTGGCTCCAGCTCAGGGACAACAG<br>TCACGTTGACCATCAGTGGAGTCCAGGCAGAAGA<br>CGAGGCTGACTATTATTGTCAATCAGTAGACAGCA<br>GTGATACTTCTGTGGTTTTCGGCGGAGGGACCAAG<br>CTGACCGTCCTAGGT |
| PD10 | VH<br>(SEQ ID NO: 39) | CAGGTGCAGCTGGTGGAGTCTGGGGGAGGCTTGG<br>TACAGCCTGGAGGGTCCCTGAGACTCTCCTGTGC<br>AGCCTCTGGATTCACCTTTGATGAACATGCCATGC<br>ACTGGGTCCGGCAAGCTCCAGGGAAGGGCCTGCA<br>GTGGGTCTCAGGAATCAATTGGAATAGTGGTAAAA<br>CAGGCTATGCGGACTCTGTGAAGGGCCGATTCACC<br>ATCTCCAGAGACAACAGCAAAAACTCCCTGTATCT<br>GCAAATGAACAGTCTGAGAGCCGAGGACACGGCC<br>GTGTATTACTGTACTAGACCCGGGGAGGACACCGG<br>GGGTGGCTTTGATATCTGGGGCCAAGGGACAATGA<br>TCACCGTCTCCTCA |
| | VL<br>(SEQ ID NO: 43) | AATTTTATGCTGACTCAGCCCGCCTCCGTGTCTGG<br>GTCCCCTGGACAGTCGATCACCATCTCCTGCACTG<br>GAAGCAGCAGCGACGTTGGTGGTTATAACTATGTC<br>TCCTGGTACCAACAGCACCCAGGCAAAGCCCCCC<br>AACTCATCATTTATGATGTCACTAAGCGGCCCTCA<br>GGGGTTTCTAATCGCTTCTCCGGCTCCAAGTCTGG<br>CAACTCGGCCTCCCTGACCATCTCTGGACTCCAGG<br>CTGAGGACGAGGCTGATTATTACTGCAGCTCATAC<br>AGCAGCAGCACTTTTTACGTCTTCGGAACTGGGA<br>CCAAGGTCACCGTCCTAGGT |

The present disclosure may include a conjugate in which a toxin, a drug, or the like is joined to the antibody. The toxin or drug may include any target compound. Examples of such toxins may be duocamycin, calicheamicin, mytansine or auristatin, and the compounds may be a known anti-cancer or anti-tumor compound such as taxol, etoposide, tenofoside, vincristine, doxorubicin, etc., alkylating agents (such as cisplatin, anthracycline (e.g., doxorubicin), etc.). The conjugates may be prepared using linker using technology available in the pertinent art.

In addition, in addition to the antibody, the present disclosure may include a bispecific binding molecule including two or more different binding sites in which a peptide, a protein or an antibody is bound to the other antigen binding sites that are different from the antibody. The bispecific binding molecule may be prepared by linking a binding specific part using the methods known in the pertinent art. In addition, when the antibody is linked, it may be linked via a sulf-hydryl link at the C-terminal region of the heavy chain. According to circumstances, it may be coded in the same vector and expressed in the same host cell to be combined.

Preparation Method of the Antibody

In another aspect, the present disclosure relates to a vector comprising the nucleic acid. For expression of antibodies or antibody fragments thereof, DNA coding the partial or full length of light chains and heavy chains may be obtained by standard molecular biology technology (e.g., PCR amplification or cDNA cloning using hybridomas expressing the target antibody), and may be inserted into an expression vector in such a way that DNA is operably bound to transcriptional and translational control sequences.

The term "operably bound" used in the present specification may mean that the antibody gene is ligated into a vector so that the transcriptional and translational control sequences in the vector serve the intended function of regulating the transcription and translation of the antibody gene. The expression vector and expression control sequences are selected so as to be compatible with the host cell used for expression. The light chain gene of the antibody and the heavy chain gene of the antibody are inserted into separate vectors, or both genes are inserted into the same expression vector. The antibody is inserted into the expression vector by standard methods (e.g., ligation of complementary restriction enzyme sites on the antibody gene fragment and vector, or blunt end ligation if no restriction enzyme site is present). According to circumstances, the recombinant expression vector may code a signal peptide that facilitates secretion of the antibody chain from the host cell. The antibody chain gene may be cloned into a vector such that the signal peptide is bound to the amino terminus of the antibody chain gene to fit to the frame. The signal peptide may be an immunoglobulin signal peptide or a heterologous signal peptide (e.g., a signal peptide derived from a protein other than an immunoglobulin). In addition, the recombinant expression vector has a "regulatory sequence" that controls the expression of the antibody chain gene in the host cell. The "regulatory sequences" may include promoters, enhancers and other expression control elements (e.g., polyadenylation signals) that control transcription or translation of an antibody chain gene. Those skilled in the art may recognize that the design of an expression vector may be varied by selecting different regulatory sequences depending on factors such as the selection of a host cell to be transformed, the level of expression of the protein, and the like.

The present disclosure may also include a host cell comprising the nucleic acid or the vector. The nucleic acid or the vector is transfected. Various types of technologies commonly used to introduce exogenous DNA into prokaryotic or eukaryotic host cells to be "transfected," for example, electrophoresis, calcium phosphate precipitation method, DEAE-dextran transfection or lipofection can be used. The antibody according to the present disclosure may be expressed in a eukaryotic cell, preferably a mammalian host cell, in consideration of the possibility of being applied to a mammalian cell. Suitable mammalian host cells for expression of the antibodies include Chinese hamster ovary (CHO) cells (including, for example, dhfr-CHO cells used together with DHFR selectable markers), NSO myeloma cells, COS cells or SP2 Cells, and the like.

In another aspect, the present disclosure relates to a preparation method of the antibody comprising culturing a host cell to express the antibody. When the recombinant expression vector coding the antibody gene is introduced into a mammalian host cell, the antibody may be prepared by culturing the host cell for a period of time sufficient to allow the antibody to be expressed in the host cell, or more preferably, for a period of time sufficient to allow the antibody to be secreted into the culture medium in which the host cell is cultured. In addition, the antibody may be prepared by comprising the biopanning using EGFRvIII comprising the amino acid sequence of SEQ ID NO: 1.

According to circumstances, the expressed antibody may be separated from the host cell and purified to be homogenous. The separation or purification of the antibody may be carried out by separation and purification methods used in the conventional proteins, for example, chromatography. The chromatography may include, for example, affinity chromatography including a protein A column, a protein G column, ion exchange chromatography or hydrophobic chromatography. In addition to the chromatography, the antibody may be further separated and purified by combining filtration, ultrafiltration, salting out, dialysis, and the like.

Pharmaceutical Composition

In another aspect, the present disclosure relates to a pharmaceutical composition for treating a cancer or a tumor comprising the antibody as an active ingredient.

The term "cancer or tumors" used in the present specification is not particularly limited as long as it is the type of cancer or tumors that can be treated by the antibody of the present disclosure. For example, it may be breast cancer, lung cancer or anal cancer caused by the overexpression of EGFRvIII, and a brain tumor, for example, a primary brain tumor (i.e., occurs in the brain) and a secondary or metastatic brain tumor.

According to circumstances, the antibody according to the present disclosure may be administered in combination with other anti-cancer drugs (i.e., before, during, or after receiving treatments for cancer). It may be administered in combination with any one or more chemotherapeutic drugs known to those skilled in the art, such as alkylating agents such as carmustine, chlorambucil, cisplatin, carboplatin, oxyplatin, proccarbazine, and cyclophosphamide; antimetabolites such as fluorouracil, phloxuridine, fludarabine, gemcitabine, methotrexate and hydroxyurea; natural products such as plant alkaloids or antibiotics such as bleomycin, doxorubicin, daunorubicin, idarubicin, etoposide, mitomycin, mitoxantrone, vinblastine, vincristine, and taxol (paclitaxel) or related compounds such as Taxotere®; therapeutic agents for treatment of brain tumors such as Gliadel® wafers containing temozolomide or carmustine; and other drugs such as irinotecan, gleevec, and the like. In addition, other biological agents such as monoclonal antibodies such as Herceptin™ for HER2 antigen, Avastin™ for VEGF, antibodies against EGF receptor, such as Erbitux®, and other EGF receptor antagonists may be included.

The pharmaceutical composition may be formulated to include a pharmaceutically acceptable carrier. The term "pharmaceutically acceptable carrier" refers to a carrier or diluent that does not stimulate living organisms and does not inhibit the biological activity and characteristics of the administered compound. The pharmaceutical carrier that is acceptable for the composition to be formulated into a liquid solution is suitable for sterilization and living bodies, and may be used by mixing a saline solution, sterile water, a Ringer's solution, a buffered saline solution, an albumin injection solution, a dextrose solution, a malto dextrin solution, glycerol, ethanol, and one or more components of these components. If necessary, the other common additives such as an antioxidant, a buffer, and a bacteriostatic agent may be added. In addition, diluents, dispersants, surfactants, binders and lubricants may be additionally added to be formulated into formulations for injection, pills, capsules, granules or tablets such as aqueous solutions, suspensions, emulsions and the like.

The pharmaceutical composition may be of various oral or parenteral formulations. In the case of formulation, it may be prepared using diluents or excipients such as fillers, extenders, binders, wetting agents, disintegrating agents, surfactants and the like which are usually used. Solid preparation for oral administration include tablets, pills, powders, granules, capsules and the like, and may be prepared by mixing one or more excipients such as starch, calcium carbonate, sucrose or lactose, gelatin, and the like with one or more compounds. In addition, in addition to the simple excipients, lubricants such as magnesium stearate, talc, and the like may also be used. Examples of the liquid preparation for oral administration include suspensions, solutions, emulsions and syrups. In addition to water and liquid paraffin, which are commonly used and are simple diluents, various excipients such as wetting agents, sweeteners, air freshener, preservatives and the like may be included.

Formulations for parenteral administration may include sterilized aqueous solutions, non-aqueous solutions, suspensions, emulsions, lyophilized formulations, and suppositories. Examples of the non-aqueous solvent and suspension solvent include propylene glycol, polyethylene glycol, vegetable oil such as olive oil, and injectable ester such as ethyl oleate. As a suppository base, witepsol, macrogol, tween, cacao butter, laurinum, glycerogelatin and the like may be used.

The pharmaceutical composition may have any one of formulations selected from the group consisting of tablets, pills, powders, granules, capsules, suspensions, solutions, emulsions, syrups, sterilized aqueous solutions, non-aqueous solvents, suspensions, emulsions, lyophilized formulations, and suppositories. In addition, they may be administered once or many times. At this time, the composition may be administered in the form of a liquid preparation, a powder, an aerosol, a capsule, an intravaginal tablet, a capsule, or a suppository. Routes of administration may include, but are not limited to, intraperitoneal, intravenous, intramuscular, subcutaneous, endothelial, oral, topical, intranasal, intrapulmonary, intrarectal, and the like. However, upon oral administration, the peptide must be formulated so as to protect it against degradation in the stomach or coating of the active agent since it is digested. In addition, the active substance may be administered by any device capable of migrating to the target cell.

The composition may be administered in a therapeutically effective amount, and a "therapeutically effective amount" may refer to an amount sufficient to treat a disease at a reasonable benefit/risk ratio applicable to medical treatment. Effective dose levels are determined by the elements including the type and severity of the individual, age, gender, type of cancer, drug activity, sensitivity to drug, time of administration, route of administration and rate of release, duration of treatment, drugs used simultaneously, and the other elements well known in the field of medicine. It may be administered in high doses of usually 0.1 to 5 mg/kg, for example 1, 2, 3 or 4 mg/kg, 10 mg/kg or 15 or 20 mg/kg. As a fixed unit capacity, for example, it may be provided with 50, 100, 200, 500 or 1000 mg. In order to cause regression of cancer or tumor, more preferably to remove tumor, it may be administered once to eight times (e.g., 1, 2, 3, 4, 5, 6, 7 or 8), or 10, 20 or more times. Based on a half-life of the antibody, it may be administered twice a week, every week, every two weeks, every month or at the other intervals of one week, two weeks, four weeks, eight weeks, three to six months, or longer.

Hereinafter, the present disclosure will be described in more detail by way of examples. It is apparent to a person having ordinary skill in the pertinent art that these examples merely illustrate the present disclosure, and the scope of the present disclosure is not limited to these examples.

Example 1: Establishment of EGFRvIII Cell Line

The EGFRvIII gene containing HindIII and XbaI restriction enzyme sites was obtained by using DNA synthesis (Invitrogen, SEQ ID NO: 1) and split by using HindIII and XbaI restriction enzymes. The split template DNA was cloned into the expression vector pcDNA3.1 split with HindIII and XbaI restriction enzymes to combine pcDNA3.1-EGFRvIII. PcDNA3.1-EGFRvIII was transformed into DH5α E. coli to select ampicillin-resistant strains. Whether the EGFRvIII gene is inserted by splitting with HindIII and XbaI restriction enzymes was confirmed.

Figure 6A:
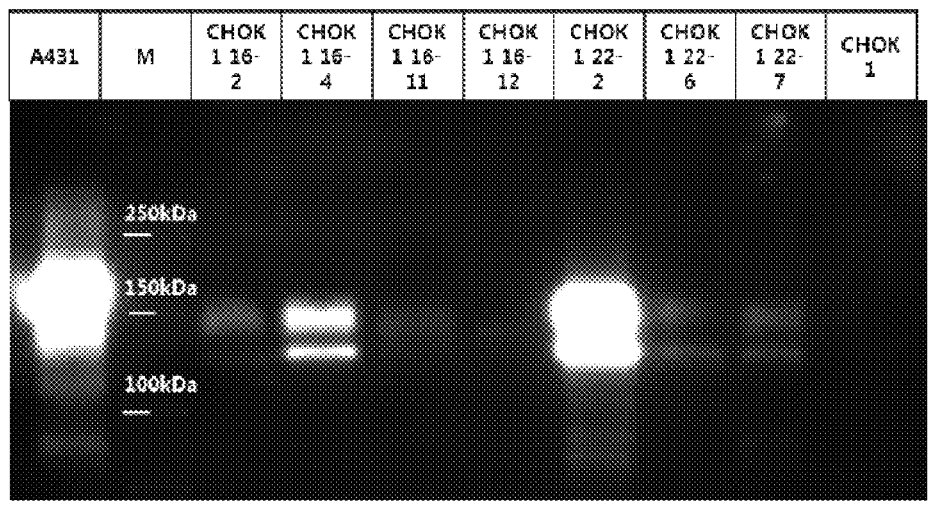
FIG. 6a illustrates Western blot results illustrating the receptor expression of a CHOK1-EGFRvIII single cell line.
Figure 6B:
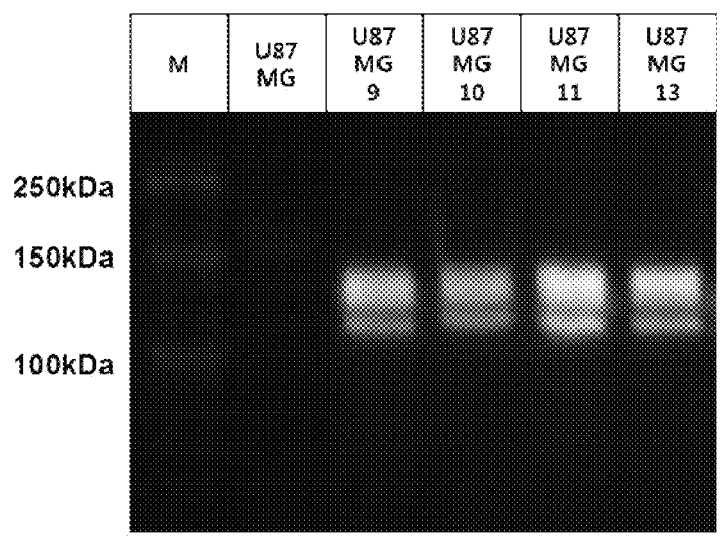
FIG. 6b illustrates Western blot results illustrating the receptor expression of a U87MG-EGFRvIII single cell line.

The pcDNA3.1-EGFRvIII vector prepared to produce the EGFRvIII cell line was transfected by using Lipofectamine 2000 with respect to CHOK1, U87MG, and A431, and the cells were cultured in 10% FBS, DMEM for 48 hours. After the cultured cells were cultured in DMEM or RPMI to which G418 of 10% FBS 1000 μg/ml, 400 μg/ml, 400 μg/ml in a 1:10 dilution, the cells to be colonized were selected and proliferated in a 6-well. When western blot was performed after each cell proliferated for 12 days was dissolved and was subject to electrophoresis, it was treated with anti-EGFR antibody and anti-human IgG HRP and reacted with ECL substrate (FIGS. 6a and 6b).

Example 2: Biopanning

The EGFRvIII peptide used as an antigen was synthesized to contain a specific sequence 13mer and a 4mer and a biotin used as a linker (SEQ ID NO: 2). The biotin-TTACCDRII peptide was also synthesized (SEQ ID NO: 3) as a negative antigen to block non-specific binding. Each peptide was prepared using a M-280 streptavidin (Invitrogen, USA) bead to join 7.8 ng of peptide per 5 μl.

The human antibody phage library was reacted with TTACCDRII peptide joined to the bead in advance at 25° C. for 30 minutes to induce binding of a non-specific phage antibody. Thereafter, the TTACCDRII peptide bound to the bead was harvested using a magnetic bar and then only supernatant liquid was taken separately. The supernatant liquid was added to the EGFRvIII peptide bound to the bead again and reacted at 25° C. for 2 hours to occur binding of an antibody phage. The EGFRvIII peptide bound to the bead was harvested using a magnetic bar and phage supernatant liquid was removed. The bead EGFRvIII peptide drawn on the magnetic bar was washed repeatedly 5 times with PBST (PBS containing 0.1% Tween 20), and finally, it was washed once with PBS. 100 ul of 100 mM triethylamine solution was reacted for 10 minutes to allow the phage bound to the antigen to elute, and the eluted phage was neutralized by 50 ul of 1M Tris pH 7.5.

The neutralized phage eluate was added to 10 ml of mid-log phase XL1-Blue E. coli cell line and reacted at 37° C. for 30 minutes to induce infection. The infected XL1-Blue E. coli cell line was spread on a 2×YT/C plate containing 1% glucose and cultured at 30° C. for 16 hours. The first panning and the second and third panning were performed in the same way.

Example 3: Selection of Phage Antibody Specifically Binding to EGFRvIII

E. coli clones were randomly selected from the completed panning, and cultured in a 96 well plate at 37° C. and 300 rpm on a mid-log phase by adding 500 μl of 2×YT/C medium, followed by addition of M13 helperphage, and then, infection of phage was induced at 37° C. for 30 minutes. The infected *E. coli* clones were cultured for 15 hours under the condition of 30° C. and 30 rpm to prepare the phage-antibody to elute. Cells of the cultured *E. coli* clones were centrifuged at 6000 rpm for 10 minutes to remove the cells and only supernatant was obtained.

Figure 7:
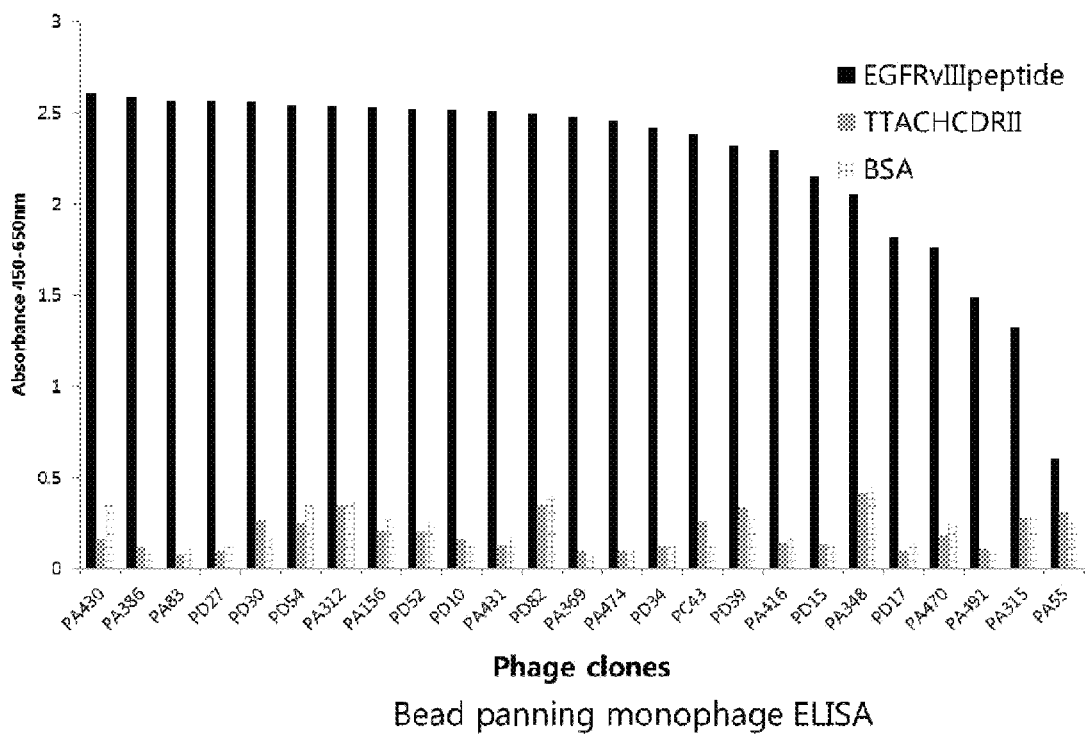
FIG. 7 illustrates the bead panning monophage ELISA results for peptides containing the EGFRvIII specific sequence used to select EGFRvIII antibodies.

EGFRvIII peptide, TTACCDRII peptide, and BSA were coated on a Maxisorb 96 well ELISA plate (Nunc, Denmark) at 1 μg/ml, blocked with 3% defatted milk/PBS for 1 hour at room temperature, and then inoculated with the obtained supernatant liquid and reacted for 1 hour at room temperature. The ELISA plate was washed three times with 0.05% of PBST, and then an anti-M13-HRP (Horse Radish Peroxidase) antibody (GE) was diluted to 1:300 PBST 0.05% for 1 hour. After treating for 10 minutes and color-developing TMB substrate (BD, USA), the reaction was stopped by treating 2N $H_2SO_4$. The color-developed ELISA was measured for absorbance at 450 nm-650 nm using a Sunrise ELISA reader (TECAN, Switzerland) (FIG. 7).

Example 4: Western Blot

EGFRvIII binding capacity by phage-antibody was observed by western blot using CHOK1-EGFRvIII cell lysate.

CHOK1 22-2, which is a CHOK1-EGFRvIII cell line prepared in Example 1, and A431 expressing CHOK1 and EGFR wildtype as a parent cell therefor were washed with PBS and dissolved by using an eluting buffer of 1% SDS, 1 mM Na3VO3, 10 mM Tris (pH 7.4), 1 mM PMSF, 10 μM Leupeptin, 1.5 μM pepstein, and 10 μg/ml aprotinin. After 15 μg of each cell lysate was separated by 6% SDS-PAGE, the protein was transferred to PVDF membrane. After 1 hour block with 3% skim milk TBST, $5 \times 10^{10}$ pfu of PA430 phage and PD54 phage were treated for 1 hour, followed by dilution of anti-M13-HRP (Horse Radish Peroxidase) antibody (GE) to 1:24000 TBST for 1 hour, and after color-development by using ECL (GE Healthcare, USA) substrate, and blot was confirmed with an Odyssey Fc imaging system (Licor, USA).

Figure 8:
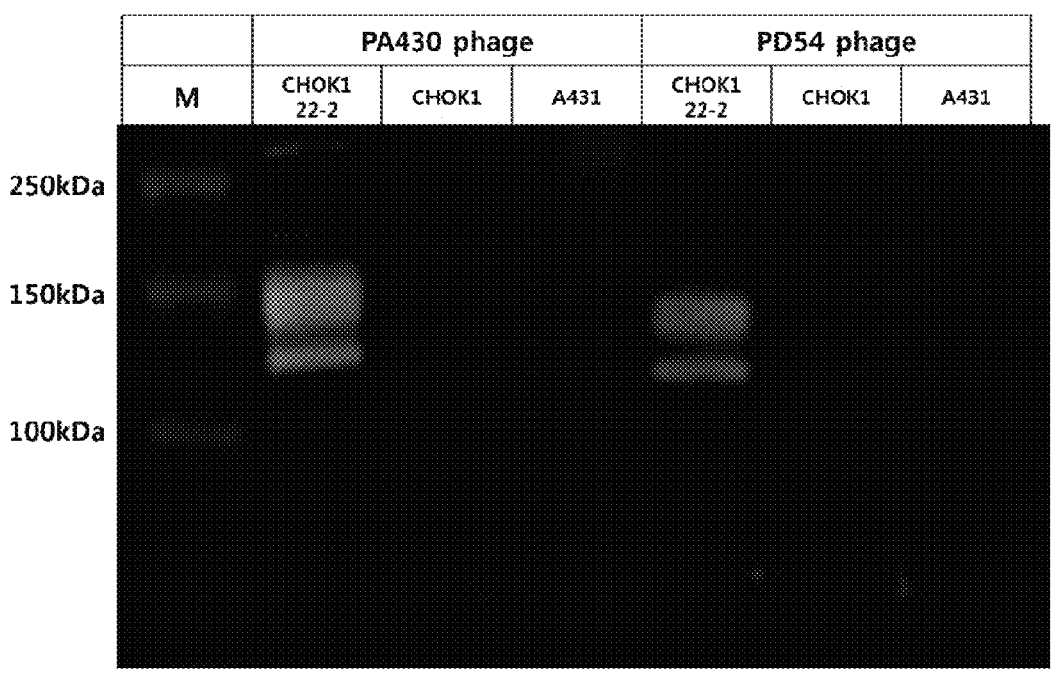
FIG. 8 illustrates Western blot results confirming the antigen-specific binding capacity of a single phage-antibody selected by bead panning.

The results are illustrated in FIG. 8, and referring to FIG. 8, it can be understood that PA430 phage and PD54 phage bind only in the cell line expressing EGFRvIII.

Example 5: IgG Expression and Purification

The conversion to the IgG form was accomplished by double-cutting with a sfiI restriction enzyme containing a variable heavy chain of the phage-antibody to obtain a fragment, and by double-cutting with a sfiI restriction enzyme in pIgGHD-6A6Hvy, which is a vector comprising a heavy chain region to obtain a ligation with a fragment.

The fragment was obtained by double-cutting with a BstX I restriction enzyme including a variable light chain of a phage-antibody. The fragment was ligated with the fragment in the same manner as the vector pIgGLD-6A6Lgt including the light chain region (as for the above method, please refer to Korean Patent Laid-Open Publication No. 2008-0109417).

The expression of IgG was determined by inoculating HEK293T cells with $8 \times 10^6$ cells per 100 mm cell culture dish and culturing the cells in a 37° C. $CO_2$ 5% culture medium for 24 hours so that the adherence and density of cells become 80-90% to culture cells. The cells were cultured with 80% to 90%.

10 μg of the heavy chain expression vector and 10 μg of the light chain expression vector of the prepared IgG, i.e., a total of 20 μg of the vector were mixed with PEI at a ratio of 1:3 (DNA:PEI) μg and react for 15 minutes to form a complex. DNA PEI complex was added to the cultured cells, and after reaction for 10 hours, it was washed with DMEM once. Then, by adding 10 ml of a culture medium to which 10% penicillin streptomycin (GIBCO, USA) is added to Freestyle 293 (GIBCO, USA), it was left alone for 48 hours to take the supernatant in which IgG was expressed.

The obtained supernatant was injected into a protein A column (GE healthcare, USA) equilibrated with 20 mM Tris-HCl, 50 mM NaCl and 5 mM EDTA pH 7.0, and washed with 50 mM Tris-HCl (pH 7.0), 5 mM EDTA, 500 mM NaCl, 0.2% Polysorbate 20, and then eluted with 50 mM NaCl, 0.1 M glycine-HCl (pH 3.5) solution. Then, the affinity chromatography neutralized with 1M Tris was performed. The eluted proteins were packed in a MWCO 10,000 spectra/por dialysis membrane (spectrum, USA), and the solutions were exchanged by PBS dialysis.

Figure 9A:
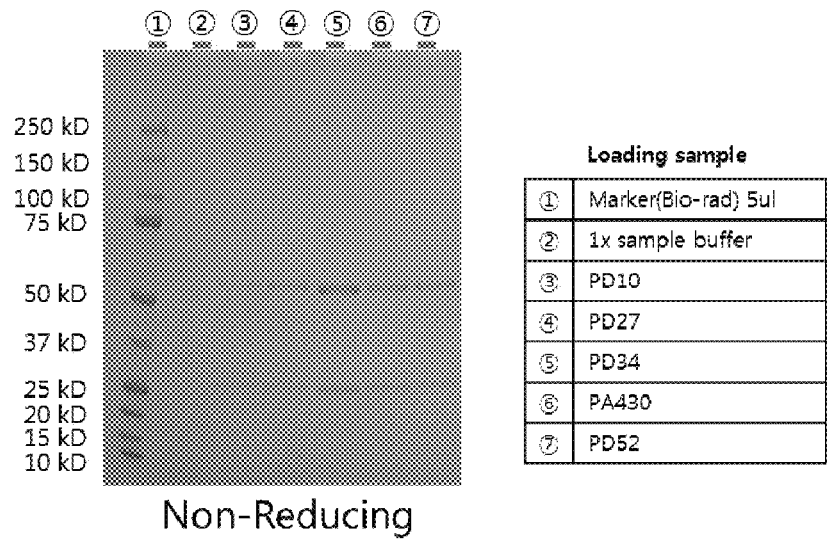
FIG. 9a illustrates the result of confirming IgG obtained by treatment in a non-reducing buffer through SDS-PAGE.
Figure 9B:
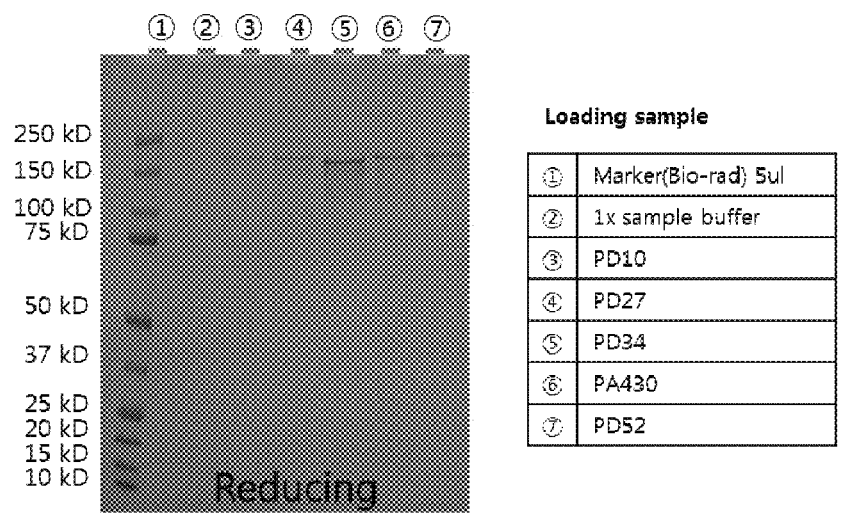
FIG. 9b illustrates the result of confirming IgG obtained by treatment in a reducing buffer through SDS-PAGE.

The results are illustrated in FIGS. 9a and 9b. With reference to FIGS. 9a and 9b, each antibody was treated with a non-reducing or reducing LDS sample buffer (Invitrogen, USA) via SDS-PAGE, and when it is loaded onto Nupage 4-12% Bis-Tris Gel (Invitrogen, USA), IgG including a 50 kDa heavy chain and a 25 kDa light chain and corresponding to 150 kDa was obtained.

Example 6: Selection of IgG Specifically Binding to EGFR vIII

ELISAs were performed to identify antigen-specific binding capacity of clones converted to IgG EGFRvIII peptide, TTACCDRII peptide and BSA were coated on 1 μg/ml 96 well plates at 37° C. for 2 hours. Thereafter, after blocking the uncoated portion with 3% skim milk/0.05% PBST, 1 μg/ml IgG was added to the plate and reacted at 37° C. for 1 hour. Anti-human IgG HRP (pierce, USA) was diluted in 1:3000 and reacted for 1 hour. Next, the TMB substrate (BD, USA) was treated for 10 minutes for color development, and the reaction was stopped by treating with 2N H2SO4. As to the color developed ELISA, the absorbance was measured at 450 nm-650 nm using a Sunrise ELISA reader (TECAN, Switzerland).

Figure 10:
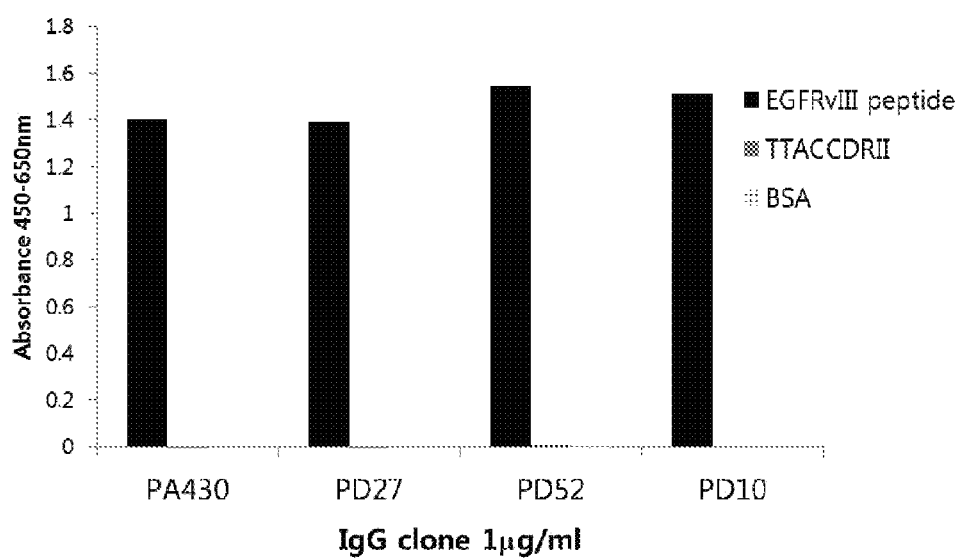
FIG. 10 illustrates the anti-EGFRvIII-peptide binding of human IgG clones using ELISA.

The results are illustrated in FIG. 10, and referring to FIG. 10, PA430, PD27, PD52 and PD10 showed specific binding capacity only in EGFRvIII peptide without nonspecific binding.

Based on these results, fluorescent dyed flow cytometry was performed to confirm whether the binding capacity of EGFRvIII-expression cell line was maintained with respect to the above-mentioned four types of antibodies. EGFRvIII expression cell line, CHOK1 22-2 and its mother cell, CHOK1, and A431, which expresses EGFR wild type were the objects. Each cell was obtained at $1 \times 10^6$ cell number, diluted with 1 μg/ml of each antibody in PBS added with 2% FBS and added to cells, and reacted at 4° C. for 1 hour. The anti-human IgG PE (Bethyl, USA) was diluted 1:200 and reacted at 4° C. for 45 minutes for fluorescence staining. Each sample was measured for $1 \times 10^4$ cells per sample using an FACS Caliber (BD, USA) instrument.

Figure 11:
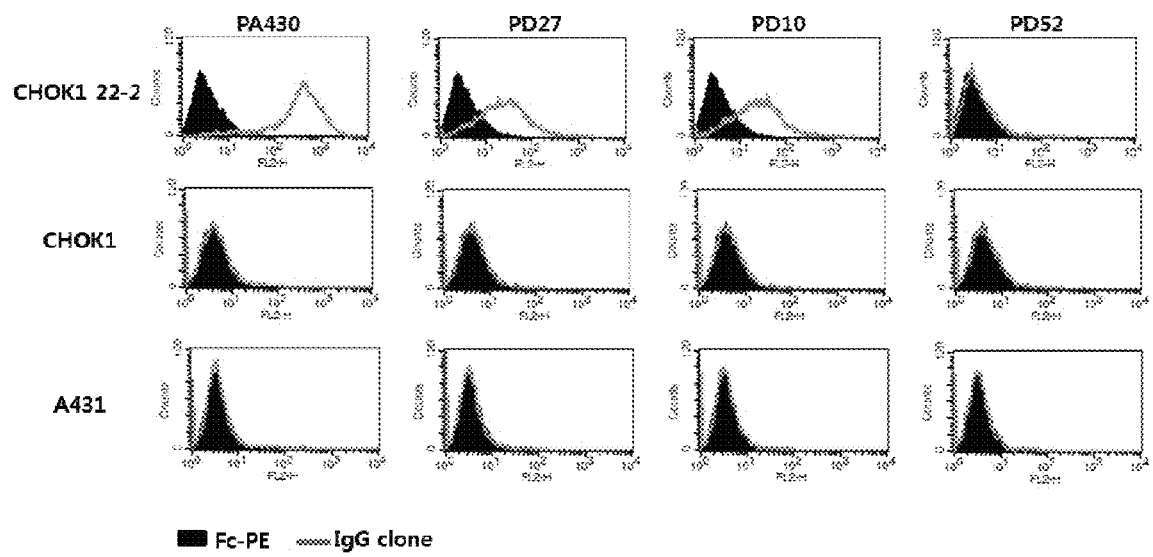
FIG. 11 illustrates the binding specificity to the EGFRvIII cell line of a human IgG clone using flow cytometry.

The results are illustrated in FIG. 11. Referring to FIG. 11, PA430, PD27, and PD10 were able to bind to EGFRvIII expression cell line CHOK1 22-2, but not to EGFRvIII non-expression cell lines CHOK1 and A431. In addition, it was shown that binding was not observed in A431, a cell expressing EGFR wild type.

In order to confirm the binding characteristics of three antibodies showing binding capacity to the EGFRvIII expression cell line according to the decrease of the antibody concentration, the following experiment was performed. The antibody concentration was diluted double the amount in a sequential order starting from 1000 ng/ml, and was prepared up to 31 ng/ml. Fluorescence staining flow cytometry was performed in the same order as described above.

Figure 12:
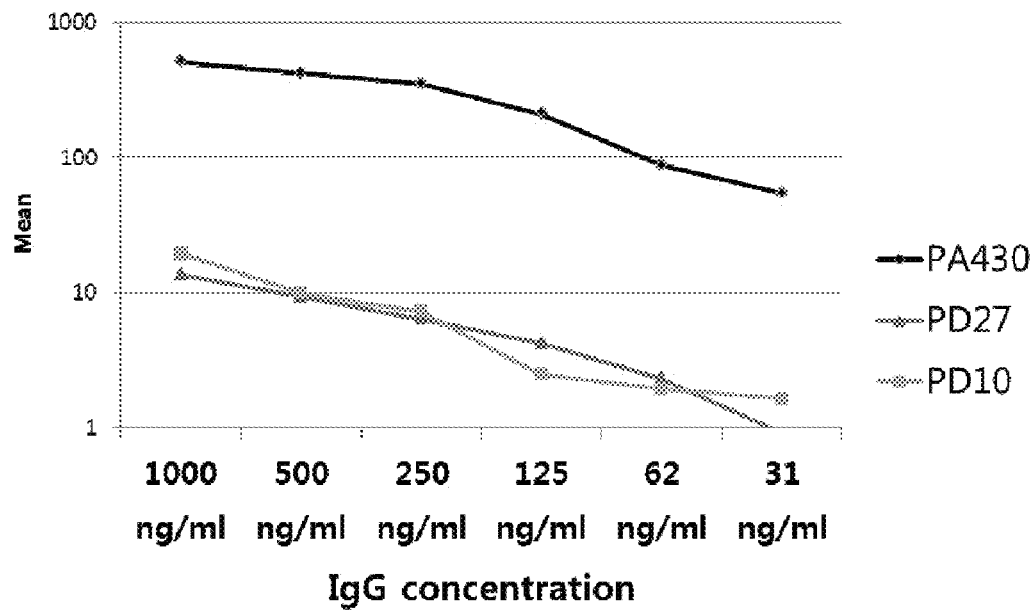
FIG. 12 illustrates the results of confirming the binding capacity affected by the concentration reduction of human IgG in the anti-EGFRvIII flow cytometry.

The results are illustrated in FIG. 12. Referring to FIG. 12, it has been observed that PA430 showed high binding capacity even at the time of treating IgG in the same concentration as compared to PD27 and PD10.

Example 7: Change in Light Chain for Affinity Enhancement

The light chain was changed to enhance the antigen specific affinity of PA430. Upon reviewing the CDRs of the variable light chains of PA430, PD52 and PD27, it has been confirmed that they are similar in sequence of the variable light chain of PA430, which has high antigen specific affinity (see Table 1-3). Using this fact, in addition to the original light chain of PA430, the light chain vector of PD52, PD27 and PD10 was mixed with the heavy chain vector of PA430 and transfected to produce IgG, which is the same as in Example 5.

Figure 13:
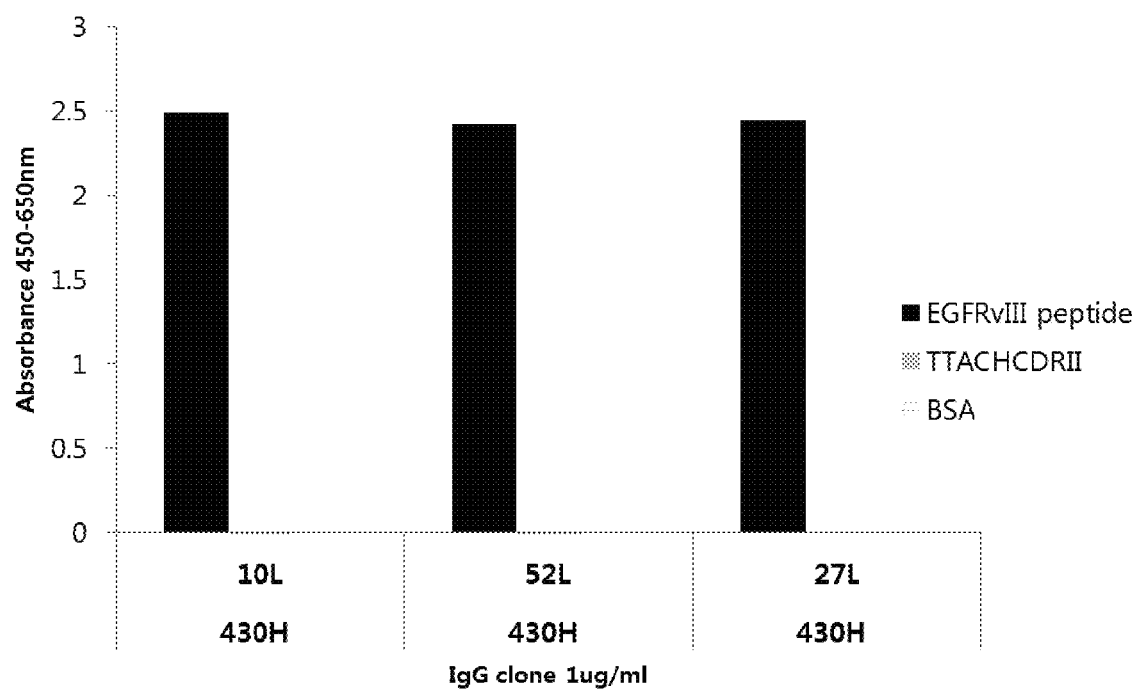
FIG. 13 illustrates the results of confirming the binding capacity according to the change in a light chain of human IgG by ELISA.

When the produced and identified 430H10L, 430H52L, and 430H27L were performed in the same manner as in the ELISA of Example 6, it was confirmed that the antigen-specific binding capacity was maintained (FIG. 13).

Figure 14:
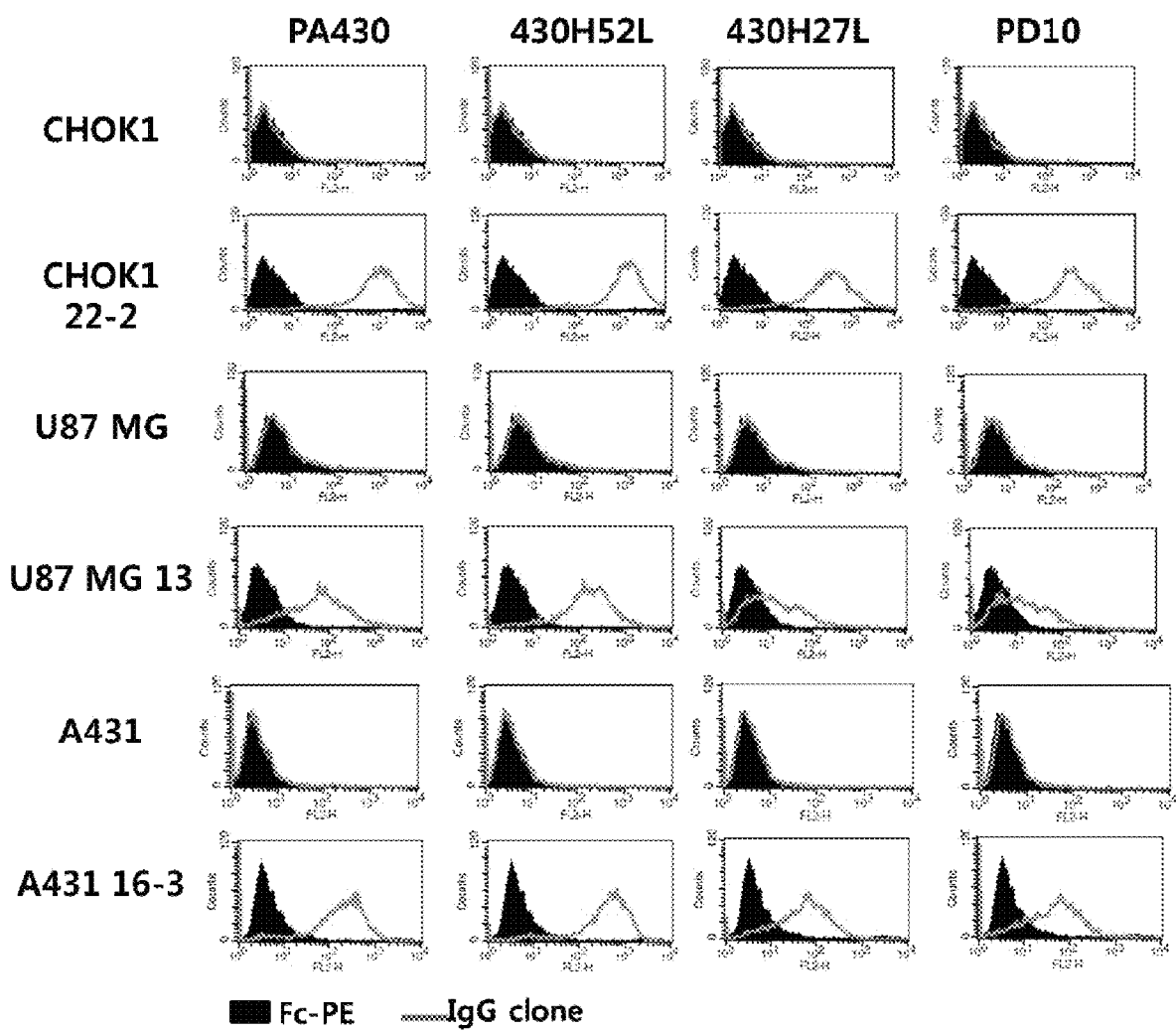
FIG. 14 illustrates the results of confirming the binding capacity according to the change in a light chain of human IgG by flow cytometry.

The fluorescent staining flow cytometry of Example 6 was performed for PA430 and 430H52L, 430H27L and PD10 IgG in the same way. When U87 MG 13 cell lines produced as EGFRvIII expression cell lines based on U87MG cells and A431 16-3 cell lines produced as EGFRvIII expression cell lines based on A431 cells were additionally performed, it has been confirmed that 430H52L and 430H27L maintains binding capacity even in the EGFRvIII specific cell line. In addition, it has been observed that 430H52L is excellent in binding signal even at the time of treating the same concentration as compared to the PA430 with a circular light chain (FIG. 14).

Example 8: Analysis of Antibody Internalization Using Fluorescent Staining Flow Cytometry By using a 430H52L antibody with EGFRvIII specific binding capacity, fluorescence staining flow cytometry was performed in order to confirm whether internalization is performed by antibody-EGFRvIII binding.

$2 \times 10^6$ cells were treated with Trypsin EDTA for U87 MG 13 cells and CHOK1 22-2 cells and then cooled at 4° C. for 30 minutes to inhibit cell activity. The cells were treated with 1 μg/ml of 430H52L in DMEM medium to induce antibody antigen binding at 4° C. for 30 minutes. The samples treated with only secondary antibody treat DMEM only. Next, after centrifugation at 1300 rpm for 3 minutes, the cells were washed with PBS to remove residual antibody, added as DMEM medium, and reacted with a sample reacting at 4° C. and an incubating sample at 37° C. for 15 minutes, 37° C. at 30 minutes, and 37° C. for 60 minutes $CO_2$ 5%. After centrifugation, the cells were washed with PBS at 4° C., and then 0.1M Glycine and 0.5M NaCl pH 2.2 were repeatedly treated three times for 10 minutes to artificially remove the antibodies bound to EGFRvIII on the cell surface. After centrifugation, the cells were washed with PBS and fixed with 4% paraformaldehyde (USB, USA) for 10 minutes at 4° C. Each sample was made to penetrate by 0.1% triton-100 (sigma Aldrich, USA) PBS solution at 4° C. for 10 minutes, or treated with 2% FBS PBS solution so that penetration does not occur. After centrifugation, the cells were washed with PBS and 2% FBS PBS was treated and blocked, and anti-human IgG PE (bethyl, USA) was treated in 1:400 for dyeing. Each sample was measured for $1 \times 10^4$ cells per sample using a FACS Caliber (BD, USA) instrument.

Figure 15A:
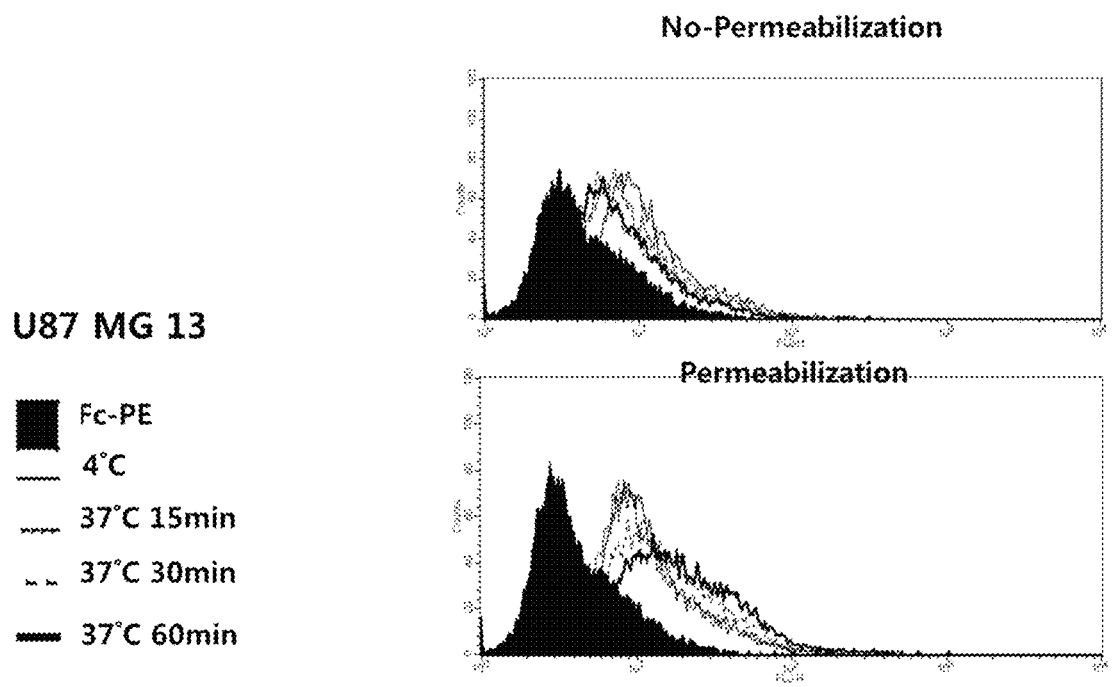
FIG. 15a illustrates the results of confirming the internalization of anti-EGFRvIII human IgG by flow cytometry using U87 MG 13.
Figure 15B:
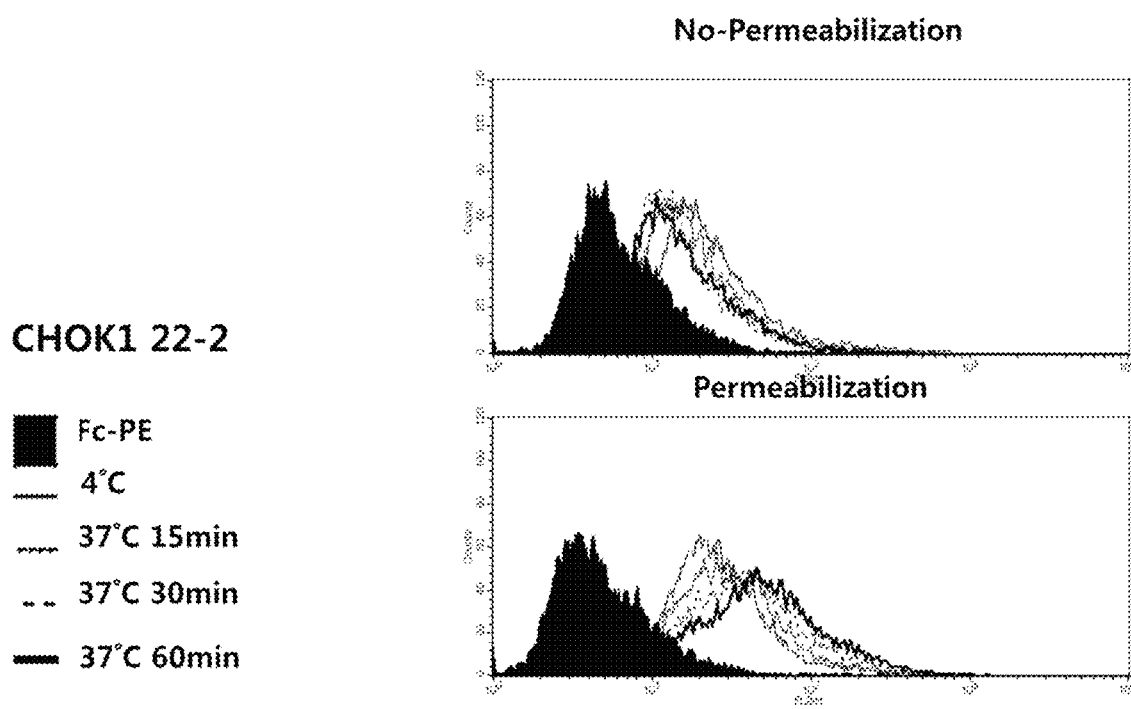
FIG. 15b illustrates the results of confirming the internalization of anti-EGFRvIII human IgG by flow cytometry using CHOK1 22-2.

The results are illustrated in FIGS. 15a and 15b, respectively. Referring to FIGS. 15a and 15b, when EGFRvIII expression cell line U87 MG 13 or CHOK1 22-2 cells were treated with 430H52L antibody and fluorescent staining was performed by using cell permeablization by going through reaction of each temperature and time, it has been observed that signal increases as time increases at 37° C. as compared to 4° C. When non-permeabilized fluorescent staining was performed in the control group without going through cell permeablization, there was no increase in signal according to increase of temperature and time. This is demonstrated by a fluorescence signal that the 430H52L IgG binds to EGFRvIII so that the internalization increases according to increase of time under the condition of 37° C.

The antibody specifically binding to EGFRvIII according to the present disclosure is a novel antibody that binds only to EGFRvIII without binding to wild type EGFR (EGFRwt), and shows excellent binding capacity in cells expressing EGFRvIII. It has been confirmed that internalization occurs, and thus it can act as an effective antagonist targeting EGFRvIII. Based thereon, the antibody specifically binding to EGFRvIII according to the present disclosure can be usefully used for the treatment of diseases induced by the expression of EGFRvIII.

Numerous variations and modifications will be apparent to a person having ordinary skill in the field to which the present disclosure pertains within the scope of the present disclosure based on the above contents.

What is claimed is:

1. An antibody binding to epidermal growth factor receptor variant III (EGFRvIII) comprising an amino acid sequence of SEQ ID NO: 1, wherein the antibody comprises the following heavy chain variable region and light chain variable region selected from the group consisting of:
   a heavy chain variable region comprising the sequence of SEQ ID NO: 28 and a light chain variable region comprising the sequence selected from the group consisting of SEQ ID NOS: 32-35;
   a heavy chain variable region comprising the sequence of SEQ ID NO: 29 and a light chain variable region comprising the sequence of SEQ ID NO: 33;
   a heavy chain variable region comprising the sequence of SEQ ID NO: 30 and a light chain variable region comprising the sequence of SEQ ID NO: 34; and
   a heavy chain variable region comprising the sequence of SEQ ID NO: 31 and a light chain variable region comprising the sequence of SEQ ID NO: 35.

2. A human antibody binding to epidermal growth factor receptor variant III (EGFRvIII) comprising an amino acid sequence of SEQ ID NO: 1, wherein the antibody comprises the following heavy chain variable region and light chain variable region selected from the group consisting of:
   a heavy chain variable region comprising the sequence of SEQ ID NO: 28 and a light chain variable region comprising the sequence selected from the group consisting of SEQ ID NOS: 32-35;
   a heavy chain variable region comprising the sequence of SEQ ID NO: 29 and a light chain variable region comprising the sequence of SEQ ID NO: 33;
   a heavy chain variable region comprising the sequence of SEQ ID NO: 30 and a light chain variable region comprising the sequence of SEQ ID NO: 34; and
   a heavy chain variable region comprising the sequence of SEQ ID NO: 31 and a light chain variable region comprising the sequence of SEQ ID NO: 35.

3. A pharmaceutical composition for treating a cancer or a tumor comprising the antibody according to claim 1 or 2 as an active ingredient.

4. A nucleic acid encoding the antibody according to claim 1.

5. The nucleic acid according to claim 4, comprising at least one sequence encoding a heavy chain variable region and selected from the group consisting of SEQ ID NOS: 36-39.

6. The nucleic acid according to claim 4, comprising at least one sequence encoding a light chain variable region and selected from the group consisting of SEQ ID NOS: 40-43.

7. A vector comprising the nucleic acid according to claim 4.

8. A cultured host cell comprising the vector according to claim 7.

9. A method of producing an antibody binding to epidermal growth factor receptor variant III (EGFRvIII) comprising an amino acid sequence of SEQ ID NO:1, comprising culturing the host cell of claim 8 for a period of time sufficient to express the antibody by the host cell, and separating and/or purifying the expressed antibody.

* * * * *

SEQUENCE LISTING

```
<160> NUMBER OF SEQ ID NOS: 43

<210> SEQ ID NO 1
<211> LENGTH: 919
<212> TYPE: PRT
<213> ORGANISM: Artificial Sequence
<220> FEATURE:
<223> OTHER INFORMATION: sequence of EGFRvIII

<400> SEQUENCE: 1
```

-continued

```
Leu Glu Glu Lys Lys Gly Asn Tyr Val Val Thr Asp His Gly Ser Cys
1               5                   10                  15

Val Arg Ala Cys Gly Ala Asp Ser Tyr Glu Met Glu Glu Asp Gly Val
            20                  25                  30

Arg Lys Cys Lys Lys Cys Glu Gly Pro Cys Arg Lys Val Cys Asn Gly
            35                  40                  45

Ile Gly Ile Gly Glu Phe Lys Asp Ser Leu Ser Ile Asn Ala Thr Asn
50                  55                  60

Ile Lys His Phe Lys Asn Cys Thr Ser Ile Ser Gly Asp Leu His Ile
65                  70                  75                  80

Leu Pro Val Ala Phe Arg Gly Asp Ser Phe Thr His Thr Pro Pro Leu
                85                  90                  95

Asp Pro Gln Glu Leu Asp Ile Leu Lys Thr Val Lys Glu Ile Thr Gly
            100                 105                 110

Phe Leu Leu Ile Gln Ala Trp Pro Glu Asn Arg Thr Asp Leu His Ala
            115                 120                 125

Phe Glu Asn Leu Glu Ile Ile Arg Gly Arg Thr Lys Gln His Gly Gln
            130                 135                 140

Phe Ser Leu Ala Val Val Ser Leu Asn Ile Thr Ser Leu Gly Leu Arg
145                 150                 155                 160

Ser Leu Lys Glu Ile Ser Asp Gly Asp Val Ile Ile Ser Gly Asn Lys
            165                 170                 175

Asn Leu Cys Tyr Ala Asn Thr Ile Asn Trp Lys Lys Leu Phe Gly Thr
            180                 185                 190

Ser Gly Gln Lys Thr Lys Ile Ile Ser Asn Arg Gly Glu Asn Ser Cys
            195                 200                 205

Lys Ala Thr Gly Gln Val Cys His Ala Leu Cys Ser Pro Glu Gly Cys
            210                 215                 220

Trp Gly Pro Glu Pro Arg Asp Cys Val Ser Cys Arg Asn Val Ser Arg
225                 230                 235                 240

Gly Arg Glu Cys Val Asp Lys Cys Asn Leu Leu Glu Gly Glu Pro Arg
            245                 250                 255

Glu Phe Val Glu Asn Ser Glu Cys Ile Gln Cys His Pro Glu Cys Leu
            260                 265                 270

Pro Gln Ala Met Asn Ile Thr Cys Thr Gly Arg Gly Pro Asp Asn Cys
            275                 280                 285

Ile Gln Cys Ala His Tyr Ile Asp Gly Pro His Cys Val Lys Thr Cys
            290                 295                 300

Pro Ala Gly Val Met Gly Glu Asn Asn Thr Leu Val Trp Lys Tyr Ala
305                 310                 315                 320

Asp Ala Gly His Val Cys His Leu Cys His Pro Asn Cys Thr Tyr Gly
            325                 330                 335

Cys Thr Gly Pro Gly Leu Glu Gly Cys Pro Thr Asn Gly Pro Lys Ile
            340                 345                 350

Pro Ser Ile Ala Thr Gly Met Val Gly Ala Leu Leu Leu Leu Leu Val
            355                 360                 365

Val Ala Leu Gly Ile Gly Leu Phe Met Arg Arg Arg His Ile Val Arg
            370                 375                 380

Lys Arg Thr Leu Arg Arg Leu Leu Gln Glu Arg Glu Leu Val Glu Pro
385                 390                 395                 400

Leu Thr Pro Ser Gly Glu Ala Pro Asn Gln Ala Leu Leu Arg Ile Leu
            405                 410                 415

Lys Glu Thr Glu Phe Lys Lys Ile Lys Val Leu Gly Ser Gly Ala Phe
```

```
              420                 425                 430
Gly Thr Val Tyr Lys Gly Leu Trp Ile Pro Glu Gly Lys Val Lys
            435                 440                 445

Ile Pro Val Ala Ile Lys Glu Leu Arg Glu Ala Thr Ser Pro Lys Ala
450                 455                 460

Asn Lys Glu Ile Leu Asp Glu Ala Tyr Val Met Ala Ser Val Asp Asn
465                 470                 475                 480

Pro His Val Cys Arg Leu Leu Gly Ile Cys Leu Thr Ser Thr Val Gln
                    485                 490                 495

Leu Ile Thr Gln Leu Met Pro Phe Gly Cys Leu Leu Asp Tyr Val Arg
                500                 505                 510

Glu His Lys Asp Asn Ile Gly Ser Gln Tyr Leu Leu Asn Trp Cys Val
            515                 520                 525

Gln Ile Ala Lys Gly Met Asn Tyr Leu Glu Asp Arg Arg Leu Val His
        530                 535                 540

Arg Asp Leu Ala Ala Arg Asn Val Leu Val Lys Thr Pro Gln His Val
545                 550                 555                 560

Lys Ile Thr Asp Phe Gly Leu Ala Lys Leu Leu Gly Ala Glu Glu Lys
                    565                 570                 575

Glu Tyr His Ala Glu Gly Gly Lys Val Pro Ile Lys Trp Met Ala Leu
                580                 585                 590

Glu Ser Ile Leu His Arg Ile Tyr Thr His Gln Ser Asp Val Trp Ser
            595                 600                 605

Tyr Gly Val Thr Val Trp Glu Leu Met Thr Phe Gly Ser Lys Pro Tyr
        610                 615                 620

Asp Gly Ile Pro Ala Ser Glu Ile Ser Ser Ile Leu Glu Lys Gly Glu
625                 630                 635                 640

Arg Leu Pro Gln Pro Pro Ile Cys Thr Ile Asp Val Tyr Met Ile Met
                    645                 650                 655

Val Lys Cys Trp Met Ile Asp Ala Asp Ser Arg Pro Lys Phe Arg Glu
                660                 665                 670

Leu Ile Ile Glu Phe Ser Lys Met Ala Arg Asp Pro Gln Arg Tyr Leu
            675                 680                 685

Val Ile Gln Gly Asp Glu Arg Met His Leu Pro Ser Pro Thr Asp Ser
        690                 695                 700

Asn Phe Tyr Arg Ala Leu Met Asp Glu Glu Asp Met Asp Asp Val Val
705                 710                 715                 720

Asp Ala Asp Glu Tyr Leu Ile Pro Gln Gln Gly Phe Phe Ser Ser Pro
                    725                 730                 735

Ser Thr Ser Arg Thr Pro Leu Leu Ser Ser Leu Ser Ala Thr Ser Asn
                740                 745                 750

Asn Ser Thr Val Ala Cys Ile Asp Arg Asn Gly Leu Gln Ser Cys Pro
            755                 760                 765

Ile Lys Glu Asp Ser Phe Leu Gln Arg Tyr Ser Ser Asp Pro Thr Gly
        770                 775                 780

Ala Leu Thr Glu Asp Ser Ile Asp Asp Thr Phe Leu Pro Val Pro Glu
785                 790                 795                 800

Tyr Ile Asn Gln Ser Val Pro Lys Arg Pro Ala Gly Ser Val Gln Asn
                    805                 810                 815

Pro Val Tyr His Asn Gln Pro Leu Asn Pro Ala Pro Ser Arg Asp Pro
                820                 825                 830

His Tyr Gln Asp Pro His Ser Thr Ala Val Gly Asn Pro Glu Tyr Leu
            835                 840                 845
```

```
Asn Thr Val Gln Pro Thr Cys Val Asn Ser Thr Phe Asp Ser Pro Ala
        850                 855                 860

His Trp Ala Gln Lys Gly Ser His Gln Ile Ser Leu Asp Asn Pro Asp
865                 870                 875                 880

Tyr Gln Gln Asp Phe Phe Pro Lys Glu Ala Lys Pro Asn Gly Ile Phe
                885                 890                 895

Lys Gly Ser Thr Ala Glu Asn Ala Glu Tyr Leu Arg Val Ala Pro Gln
                900                 905                 910

Ser Ser Glu Phe Ile Gly Ala
        915
```

<210> SEQ ID NO 2
<211> LENGTH: 18
<212> TYPE: PRT
<213> ORGANISM: Artificial Sequence
<220> FEATURE:
<223> OTHER INFORMATION: sequence of Antigen
<220> FEATURE:
<221> NAME/KEY: misc_feature
<223> OTHER INFORMATION: C-terminal biotin

<400> SEQUENCE: 2

```
Leu Glu Glu Lys Lys Gly Asn Tyr Val Val Thr Asp His Cys Ser Gly
1               5                   10                  15

Gly Lys
```

<210> SEQ ID NO 3
<211> LENGTH: 17
<212> TYPE: PRT
<213> ORGANISM: Artificial Sequence
<220> FEATURE:
<223> OTHER INFORMATION: sequence of Negative Antigen
<220> FEATURE:
<221> NAME/KEY: misc_feature
<223> OTHER INFORMATION: N-terminal biotin

<400> SEQUENCE: 3

```
Glu Ile Asn Pro Gly Asn Gly His Thr Asn Tyr Asn Glu Lys Phe Lys
1               5                   10                  15

Ser
```

<210> SEQ ID NO 4
<211> LENGTH: 5
<212> TYPE: PRT
<213> ORGANISM: Artificial Sequence
<220> FEATURE:
<223> OTHER INFORMATION: H-CDR1

<400> SEQUENCE: 4

```
Tyr His Ala Met His
1               5
```

<210> SEQ ID NO 5
<211> LENGTH: 5
<212> TYPE: PRT
<213> ORGANISM: Artificial Sequence
<220> FEATURE:
<223> OTHER INFORMATION: H-CDR1

<400> SEQUENCE: 5

```
Asp Tyr Ala Met His
1               5
```

<210> SEQ ID NO 6
<211> LENGTH: 5
<212> TYPE: PRT
<213> ORGANISM: Artificial Sequence
<220> FEATURE:
<223> OTHER INFORMATION: H-CDR1

<400> SEQUENCE: 6

Glu His Ala Met His
1               5

<210> SEQ ID NO 7
<211> LENGTH: 5
<212> TYPE: PRT
<213> ORGANISM: Artificial Sequence
<220> FEATURE:
<223> OTHER INFORMATION: H-CDR1

<400> SEQUENCE: 7

Glu His Ala Met His
1               5

<210> SEQ ID NO 8
<211> LENGTH: 17
<212> TYPE: PRT
<213> ORGANISM: Artificial Sequence
<220> FEATURE:
<223> OTHER INFORMATION: H-CDR2

<400> SEQUENCE: 8

Ala Met Ser His Asp Gly Thr Glu Thr Ser Tyr Ala Asp Ser Val Lys
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: H-CDR2

<400> SEQUENCE: 9

Gly Ile Ser Trp Asn Ser Gly Ala Ile Gly Tyr Ala Asp Ser Val Lys
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: H-CDR2

<400> SEQUENCE: 10

Gly Ile Asn Trp Asn Ser Gly Lys Thr Gly Tyr Ala Asp Ser Val Lys
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: H-CDR2

<400> SEQUENCE: 11

```
Gly Ile Asn Trp Asn Ser Gly Lys Thr Gly Tyr Ala Asp Ser Val Lys
1               5                   10                  15
Gly
```

\<210\> SEQ ID NO 12
\<211\> LENGTH: 12
\<212\> TYPE: PRT
\<213\> ORGANISM: Artificial Sequence
\<220\> FEATURE:
\<223\> OTHER INFORMATION: H-CDR3

\<400\> SEQUENCE: 12

```
Glu Gly Leu Arg Ser Asn Gly Gly Ala Phe Glu Thr
1               5                   10
```

\<210\> SEQ ID NO 13
\<211\> LENGTH: 11
\<212\> TYPE: PRT
\<213\> ORGANISM: Artificial Sequence
\<220\> FEATURE:
\<223\> OTHER INFORMATION: H-CDR3

\<400\> SEQUENCE: 13

```
Ala Ser Arg Gly Leu Gly Asp Ala Phe Asp Ile
1               5                   10
```

\<210\> SEQ ID NO 14
\<211\> LENGTH: 11
\<212\> TYPE: PRT
\<213\> ORGANISM: Artificial Sequence
\<220\> FEATURE:
\<223\> OTHER INFORMATION: H-CDR3

\<400\> SEQUENCE: 14

```
Pro Gly Glu Asp Thr Gly Gly Gly Phe Asp Ile
1               5                   10
```

\<210\> SEQ ID NO 15
\<211\> LENGTH: 11
\<212\> TYPE: PRT
\<213\> ORGANISM: Artificial Sequence
\<220\> FEATURE:
\<223\> OTHER INFORMATION: H-CDR3

\<400\> SEQUENCE: 15

```
Pro Gly Glu Asp Thr Gly Gly Gly Phe Asp Ile
1               5                   10
```

\<210\> SEQ ID NO 16
\<211\> LENGTH: 11
\<212\> TYPE: PRT
\<213\> ORGANISM: Artificial Sequence
\<220\> FEATURE:
\<223\> OTHER INFORMATION: L-CDR1

\<400\> SEQUENCE: 16

```
Ser Gly Asp Val Leu Pro Lys His Tyr Ala Tyr
1               5                   10
```

\<210\> SEQ ID NO 17
\<211\> LENGTH: 11
\<212\> TYPE: PRT
\<213\> ORGANISM: Artificial Sequence
\<220\> FEATURE:
\<223\> OTHER INFORMATION: L-CDR1

```
<400> SEQUENCE: 17

Ser Gly Asp Val Leu Pro Lys His Tyr Ala Tyr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: L-CDR1

<400> SEQUENCE: 18

Ser Gly Asp Val Leu Ala Asp His Tyr Ser Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: L-CDR1

<400> SEQUENCE: 19

Ser Ser Asp Val Gly Gly Tyr Asn Tyr Val Ser
1               5                   10

<210> SEQ ID NO 20
<211> LENGTH: 7
<212> TYPE: PRT
<213> ORGANISM: Artificial Sequence
<220> FEATURE:
<223> OTHER INFORMATION: L-CDR2

<400> SEQUENCE: 20

Lys Asp Ser Glu Arg Pro Ser
1               5

<210> SEQ ID NO 21
<211> LENGTH: 7
<212> TYPE: PRT
<213> ORGANISM: Artificial Sequence
<220> FEATURE:
<223> OTHER INFORMATION: L-CDR2

<400> SEQUENCE: 21

Lys Asp Thr Glu Arg Pro Ser
1               5

<210> SEQ ID NO 22
<211> LENGTH: 7
<212> TYPE: PRT
<213> ORGANISM: Artificial Sequence
<220> FEATURE:
<223> OTHER INFORMATION: L-CDR2

<400> SEQUENCE: 22

Lys Asp Ser Glu Arg Pro Ser
1               5

<210> SEQ ID NO 23
<211> LENGTH: 7
<212> TYPE: PRT
<213> ORGANISM: Artificial Sequence
<220> FEATURE:
<223> OTHER INFORMATION: L-CDR2

<400> SEQUENCE: 23
```

Asp Val Thr Lys Arg Pro Ser
1               5

<210> SEQ ID NO 24
<211> LENGTH: 11
<212> TYPE: PRT
<213> ORGANISM: Artificial Sequence
<220> FEATURE:
<223> OTHER INFORMATION: L-CDR3

<400> SEQUENCE: 24

Gln Ser Val Asp Ser Ser Asp Thr Ser Val Val
1               5                   10

<210> SEQ ID NO 25
<211> LENGTH: 11
<212> TYPE: PRT
<213> ORGANISM: Artificial Sequence
<220> FEATURE:
<223> OTHER INFORMATION: L-CDR3

<400> SEQUENCE: 25

Gln Ser Val Asp Asn Ser Asp Thr Ser Val Val
1               5                   10

<210> SEQ ID NO 26
<211> LENGTH: 11
<212> TYPE: PRT
<213> ORGANISM: Artificial Sequence
<220> FEATURE:
<223> OTHER INFORMATION: L-CDR3

<400> SEQUENCE: 26

Gln Ser Val Asp Ser Ser Asp Thr Ser Val Val
1               5                   10

<210> SEQ ID NO 27
<211> LENGTH: 10
<212> TYPE: PRT
<213> ORGANISM: Artificial Sequence
<220> FEATURE:
<223> OTHER INFORMATION: L-CDR3

<400> SEQUENCE: 27

Ser Ser Tyr Ser Ser Ser Thr Phe Tyr Val
1               5                   10

<210> SEQ ID NO 28
<211> LENGTH: 121
<212> TYPE: PRT
<213> ORGANISM: Artificial Sequence
<220> FEATURE:
<223> OTHER INFORMATION: Hv

<400> SEQUENCE: 28

Gln Met Gln Leu Val Glu Ser Gly Gly Val Gln Pro Gly Lys
1               5                   10                  15

Ser Leu Arg Leu Ser Cys Ala Ala Ser Gly Phe Thr Phe Ser Tyr His
                20                  25                  30

Ala Met His Trp Val Arg Gln Ala Pro Gly Lys Gly Leu Glu Trp Leu
            35                  40                  45

Ala Ala Met Ser His Asp Gly Thr Glu Thr Tyr Ala Asp Ser Val
        50                  55                  60

Lys Gly Arg Ile Thr Ile Ser Arg Asp Asn Ser Lys Ser Ala Leu Tyr

```
                65                  70                  75                  80
Leu Gln Met Asn Ser Leu Arg Ala Glu Asp Thr Ala Val Tyr Tyr Cys
                    85                  90                  95

Thr Ala Glu Gly Leu Arg Ser Asn Gly Gly Ala Phe Glu Thr Trp Gly
                100                 105                 110

Arg Gly Thr Met Ile Thr Val Ser Ser
            115                 120

<210> SEQ ID NO 29
<211> LENGTH: 120
<212> TYPE: PRT
<213> ORGANISM: Artificial Sequence
<220> FEATURE:
<223> OTHER INFORMATION: Hv

<400> SEQUENCE: 29

Gln Met Gln Leu Val Gln Ser Gly Gly Gly Val Val Gln Pro Gly Gly
1               5                   10                  15

Ser Leu Arg Leu Ser Cys Val Gly Ser Gly Phe Ser Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ala Ile Gly Tyr Ala Asp Ser Val
    50                  55                  60

Lys Gly Arg Phe Thr Val Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Thr Ala Ser Arg Gly Leu Gly Asp Ala Phe Asp Ile Trp Gly Gln
                100                 105                 110

Gly Thr Met Val Thr Val Ser Ser
            115                 120

<210> SEQ ID NO 30
<211> LENGTH: 120
<212> TYPE: PRT
<213> ORGANISM: Artificial Sequence
<220> FEATURE:
<223> OTHER INFORMATION: Hv

<400> SEQUENCE: 30

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Glu His
                20                  25                  30

Ala Met His Trp Val Arg Gln Ala Pro Gly Lys Gly Leu Gln Trp Val
            35                  40                  45

Ser Gly Ile Asn Trp Asn Ser Gly Lys Thr Gly Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                    85                  90                  95

Thr Arg Pro Gly Glu Asp Thr Gly Gly Phe Asp Ile Trp Gly Gln
                100                 105                 110

Gly Thr Met Ile Thr Val Ser Ser
            115                 120
```

```
<210> SEQ ID NO 31
<211> LENGTH: 120
<212> TYPE: PRT
<213> ORGANISM: Artificial Sequence
<220> FEATURE:
<223> OTHER INFORMATION: Hv

<400> SEQUENCE: 31

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Glu His
            20                  25                  30

Ala Met His Trp Val Arg Gln Ala Pro Gly Lys Gly Leu Gln Trp Val
        35                  40                  45

Ser Gly Ile Asn Trp Asn Ser Gly Lys Thr Gly Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Pro Gly Glu Asp Thr Gly Gly Phe Asp Ile Trp Gly Gln
            100                 105                 110

Gly Thr Met Ile Thr Val Ser Ser
        115                 120

<210> SEQ ID NO 32
<211> LENGTH: 109
<212> TYPE: PRT
<213> ORGANISM: Artificial Sequence
<220> FEATURE:
<223> OTHER INFORMATION: Lv

<400> SEQUENCE: 32

Ser Tyr Glu Leu Thr Gln Pro Pro Ser Val Ser Val Ala Pro Gly Gln
1               5                   10                  15

Thr Ala Arg Ile Thr Cys Ser Gly Asp Val Leu Pro Lys His Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Thr Gly Ser
    50                  55                  60

Ser Ser Gly Thr Lys Val Thr Leu Thr Ile Ser Gly Val Arg Ala Glu
65                  70                  75                  80

Asp Glu Ala Asp Tyr Tyr Cys Gln Ser Val Asp Ser Ser Asp Thr Ser
                85                  90                  95

Val Val Phe Gly Gly Gly Thr Lys Leu Thr Val Leu Gly
            100                 105

<210> SEQ ID NO 33
<211> LENGTH: 109
<212> TYPE: PRT
<213> ORGANISM: Artificial Sequence
<220> FEATURE:
<223> OTHER INFORMATION: Lv

<400> SEQUENCE: 33

Ser Tyr Glu Leu Thr Gln Pro Pro Ser Val Ser Val Ser Pro Gly Gln
1               5                   10                  15

Thr Ala Arg Ile Thr Cys Ser Gly Asp Val Leu Pro Lys His Tyr Ala
```

```
                    20                  25                  30

Tyr Trp Tyr Gln Gln Lys Pro Gly Gln Ala Pro Val Leu Val Ile Tyr
            35                  40                  45

Lys Asp Thr Glu Arg Pro Ser Gly Ile Pro Glu Arg Phe Ser Gly Ser
        50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Val Asp Asn Ser Asp Thr Ser
                85                  90                  95

Val Val Phe Gly Gly Gly Thr Lys Leu Thr Val Leu Gly
            100                 105

<210> SEQ ID NO 34
<211> LENGTH: 109
<212> TYPE: PRT
<213> ORGANISM: Artificial Sequence
<220> FEATURE:
<223> OTHER INFORMATION: Lv

<400> SEQUENCE: 34

Ser Tyr Glu Leu Thr Gln Pro Leu Ser Val Ser Val Ser Pro Gly Gln
1               5                   10                  15

Thr Ala Arg Ile Thr Cys Ser Gly Asp Val Leu Ala Asp His Tyr Ser
            20                  25                  30

Tyr Trp Tyr Gln Gln Lys Pro Gly Gln Ala Pro Val Leu Val Met Tyr
            35                  40                  45

Lys Asp Ser Glu Arg Pro Ser Gly Ile Pro Glu Arg Phe Ser Gly Ser
        50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Val Asp Ser Ser Asp Thr Ser
                85                  90                  95

Val Val Phe Gly Gly Gly Thr Lys Leu Thr Val Leu Gly
            100                 105

<210> SEQ ID NO 35
<211> LENGTH: 111
<212> TYPE: PRT
<213> ORGANISM: Artificial Sequence
<220> FEATURE:
<223> OTHER INFORMATION: Lv

<400> SEQUENCE: 35

Asn Phe Met Leu Thr Gln Pro Ala Ser Val Ser Gly Ser Pro Gly Gln
1               5                   10                  15

Ser Ile Thr Ile Ser Cys Thr Gly Ser Ser Asp Val Gly Gly Tyr
            20                  25                  30

Asn Tyr Val Ser Trp Tyr Gln Gln His Pro Gly Lys Ala Pro Gln Leu
            35                  40                  45

Ile Ile Tyr Asp Val Thr Lys Arg Pro Ser Gly Val Ser Asn Arg Phe
        50                  55                  60

Ser Gly Ser Lys Ser Gly Asn Ser Ala Ser Leu Thr Ile Ser Gly Leu
65                  70                  75                  80

Gln Ala Glu Asp Glu Ala Asp Tyr Tyr Cys Ser Ser Tyr Ser Ser Ser
                85                  90                  95

Thr Phe Tyr Val Phe Gly Thr Gly Thr Lys Val Thr Val Leu Gly
            100                 105                 110
```

<210> SEQ ID NO 36
<211> LENGTH: 363
<212> TYPE: DNA
<213> ORGANISM: Artificial Sequence
<220> FEATURE:
<223> OTHER INFORMATION: Hv

<400> SEQUENCE: 36

```
cagatgcagc tggtggagtc cggggaggc gtggtccagc ctgggaagtc cctgagactt      60
tcctgtgcag cgtctggatt caccttcagt taccatgcca tgcactgggt ccgccaggct    120
ccaggcaagg ggctggagtg gctggcagct atgtcacatg atggaaccga aaccagctac    180
gcagactccg tgaagggccg aatcaccatc tccagagaca attccaagag tgcgttgtat    240
ctacaaatga acagtctgag agccgaggac acggccgtgt attactgtac cgcagagggg    300
cttcggagca atggaggggc ttttgagact tggggccgcg gacaatgat caccgtctcc    360
tca                                                                   363
```

<210> SEQ ID NO 37
<211> LENGTH: 360
<212> TYPE: DNA
<213> ORGANISM: Artificial Sequence
<220> FEATURE:
<223> OTHER INFORMATION: Hv

<400> SEQUENCE: 37

```
cagatgcagc tggtgcagtc tgagggggc gtggtacagc ctgggggtc cctgagactc       60
tcctgtgtag cgtctggatt cagctttgat gattatgcca tgcactgggt ccgtcaggct    120
ccagggaagg gcctggagtg ggtctcaggt attagttgga atagtggtgc ataggctat     180
gcggactctg tgaagggccg attcaccgtc tccagagaca acagcaaaaa ctccctgtat    240
ctgcaaatga acagtctgag agccgaggac acggccgtgt attactgtgc cacagcctcc    300
agaggacttg gtgatgcttt tgatatctgg ggccaggga caatggtcac cgtctcctca    360
```

<210> SEQ ID NO 38
<211> LENGTH: 360
<212> TYPE: DNA
<213> ORGANISM: Artificial Sequence
<220> FEATURE:
<223> OTHER INFORMATION: Hv

<400> SEQUENCE: 38

```
caggtgcagc tggtggagtc tgggggaggc ttggtacagc ctggagggtc cctgagactc     60
tcctgtgcag cctctggatt cacctttgat gaacatgcca tgcactgggt ccggcaagct    120
ccagggaagg gcctgcagtg ggtctcagga atcaattgga atagtggtaa aacaggctat    180
gcggactctg tgaagggccg attcaccatc tccagagaca acagcaaaaa ctccctgtat    240
ctgcaaatga acagtctgag agccgaggac acggccgtgt attactgtac tagacccggg    300
gaggacaccg ggggtggctt tgatatctgg ggccaaggga caatgatcac cgtctcctca    360
```

<210> SEQ ID NO 39
<211> LENGTH: 360
<212> TYPE: DNA
<213> ORGANISM: Artificial Sequence
<220> FEATURE:
<223> OTHER INFORMATION: Hv

<400> SEQUENCE: 39

```
caggtgcagc tggtggagtc tggggggaggc ttggtacagc ctggagggtc cctgagactc    60
```

```
tcctgtgcag cctctggatt caccttttgat gaacatgcca tgcactgggt ccggcaagct      120
ccagggaagg gcctgcagtg ggtctcagga atcaattgga atagtggtaa aacaggctat      180
gcggactctg tgaagggccg attcaccatc tccagagaca acagcaaaaa ctccctgtat      240
ctgcaaatga acagtctgag agccgaggac acggccgtgt attactgtac tagacccggg      300
gaggacaccg ggggtggctt tgatatctgg ggccaaggga caatgatcac cgtctcctca      360
```

```
<210> SEQ ID NO 40
<211> LENGTH: 327
<212> TYPE: DNA
<213> ORGANISM: Artificial Sequence
<220> FEATURE:
<223> OTHER INFORMATION: Lv

<400> SEQUENCE: 40
tcctatgagc tgacacagcc accctcagtg tcggtggccc cagggcagac ggccaggatc      60
acctgctctg gagatgtact gccaaaacat tatgcttatt ggtaccagca gaagccaggc     120
caggcccctg ttttggtgat atataaagac agcgagaggc cctcagggat ccctgagcga     180
ttcactggtt ccagctcagg gacaaaagtc acgctgacca taagtggagt ccgggcagaa     240
gacgaggctg actattattg tcaatcagta gacagcagtg atacttctgt ggttttcggc     300
ggagggacca agctgaccgt cctaggt                                         327
```

```
<210> SEQ ID NO 41
<211> LENGTH: 327
<212> TYPE: DNA
<213> ORGANISM: Artificial Sequence
<220> FEATURE:
<223> OTHER INFORMATION: Lv

<400> SEQUENCE: 41
tcctatgagc tgacacagcc cccctcggtg tcagtgtccc caggacagac ggccaggatc      60
acctgctctg gagatgtact gccaaaacat tatgcttatt ggtaccagca gaagccaggc     120
caggcccctg ttttggtgat atataaagac actgagaggc cctcagggat ccctgagcga     180
ttctctggct ccagttcagg gacaaacgtc acgttgacca tcagtggagt ccaggcagaa     240
gacgaggctg actattattg tcaatcagta gacaacagtg atacttctgt ggttttcggc     300
ggagggacca agctgaccgt cctaggt                                         327
```

```
<210> SEQ ID NO 42
<211> LENGTH: 327
<212> TYPE: DNA
<213> ORGANISM: Artificial Sequence
<220> FEATURE:
<223> OTHER INFORMATION: Lv

<400> SEQUENCE: 42
tcctatgagc tgactcagcc actctcggtg tcagtgtccc caggacagac ggccaggatc      60
acctgctctg gagatgtatt ggcagatcat tattcttatt ggtaccagca gaagccaggc     120
caggcccctg tgttggtgat gtataaagac agtgagaggc cctctgggat ccctgagcga     180
ttctctggct ccagctcagg gacaacgtc acgttgacca tcagtggagt ccaggcagaa      240
gacgaggctg actattattg tcaatcagta gacagcagtg atacttctgt ggttttcggc     300
ggagggacca agctgaccgt cctaggt                                         327
```

```
<210> SEQ ID NO 43
```

```
<211> LENGTH: 333
<212> TYPE: DNA
<213> ORGANISM: Artificial Sequence
<220> FEATURE:
<223> OTHER INFORMATION: Lv

<400> SEQUENCE: 43
aattttatgc tgactcagcc cgcctccgtg tctgggtccc ctggacagtc gatcaccatc      60
tcctgcactg gaagcagcag cgacgttggt ggttataact atgtctcctg gtaccaacag     120
cacccaggca aagcccccca actcatcatt tatgatgtca ctaagcggcc ctcaggggtt     180
tctaatcgct tctccggctc caagtctggc aactcggcct ccctgaccat ctctggactc     240
caggctgagg acgaggctga ttattactgc agctcataca gcagcagcac ttttacgtc      300 ttcggaactg ggaccaaggt caccgtccta ggt                                  333
```